United States Patent
Sokurenko et al.

(10) Patent No.: US 10,722,580 B2
(45) Date of Patent: Jul. 28, 2020

(54) **COMPOSITIONS AND METHODS FOR TREATMENT AND PREVENTION OF UROPATHOGENIC *E. COLI* INFECTION**

(71) Applicant: UNIVERSITY OF WASHINGTON, Seattle, WA (US)

(72) Inventors: Evgeni V. Sokurenko, Seattle, WA (US); Dagmara Kisiela, Seattle, WA (US); Wendy Evelyn Thomas, Seattle, WA (US); Veronika L. Tchesnokova, Seattle, WA (US)

(73) Assignee: UNIVERSITY OF WASHINGTON, Seattle, WA (US)

( * ) Notice: Subject to any disclaimer, the term of this patent is extended or adjusted under 35 U.S.C. 154(b) by 191 days.

(21) Appl. No.: 15/573,748

(22) PCT Filed: May 13, 2016

(86) PCT No.: PCT/US2016/032495
§ 371 (c)(1),
(2) Date: Nov. 13, 2017

(87) PCT Pub. No.: WO2016/183501
PCT Pub. Date: Nov. 17, 2016

(65) Prior Publication Data
US 2018/0193457 A1  Jul. 12, 2018

Related U.S. Application Data

(60) Provisional application No. 62/208,913, filed on Aug. 24, 2015, provisional application No. 62/160,852, filed on May 13, 2015.

(51) Int. Cl.
| | | |
|---|---|---|
| *A61K 39/40* | (2006.01) | |
| *C07K 14/245* | (2006.01) | |
| *A61K 39/02* | (2006.01) | |
| *A61K 39/00* | (2006.01) | |
| *C07K 16/12* | (2006.01) | |
| *A61P 13/10* | (2006.01) | |
| *A61P 31/04* | (2006.01) | |
| *A61P 1/04* | (2006.01) | |

(52) U.S. Cl.
CPC .............. *A61K 39/40* (2013.01); *A61K 39/02* (2013.01); *A61P 1/04* (2018.01); *A61P 13/10* (2018.01); *A61P 31/04* (2018.01); *C07K 14/245* (2013.01); *C07K 16/1232* (2013.01); *A61K 2039/505* (2013.01); *A61K 2039/52* (2013.01); *C07K 2317/34* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 6,632,431 B2 | 10/2003 | Wu | |
| 6,780,969 B2* | 8/2004 | Wang | C07K 14/245 424/198.1 |
| 9,107,866 B2* | 8/2015 | Savarino | A61K 39/0258 |
| 9,636,417 B2* | 5/2017 | Rasschaert | G01N 33/573 |
| 9,814,769 B2* | 11/2017 | Ghunaim | A61K 39/0258 |
| 9,834,823 B2* | 12/2017 | Price | C12Q 1/689 |
| 9,878,037 B2* | 1/2018 | Eldridge | A61K 39/39 |
| 10,111,954 B2* | 10/2018 | Chang | A61K 38/21 |
| 10,137,192 B2* | 11/2018 | Eldridge | A61K 39/39 |
| 2003/0199071 A1* | 10/2003 | Langermann | C07K 14/245 435/200 |
| 2004/0141993 A1* | 7/2004 | Wang | C07K 14/245 424/185.1 |
| 2008/0044424 A1 | 2/2008 | Cohen et al. | |
| 2014/0134171 A1* | 5/2014 | Ghayur | A61K 45/06 424/136.1 |
| 2016/0106826 A1* | 4/2016 | Ghunaim | A61K 39/0258 424/190.1 |

(Continued)

FOREIGN PATENT DOCUMENTS

| | | | | |
|---|---|---|---|---|
| WO | WO2012047247 A3 | 4/2012 | | |
| WO | WO2012047427 A2 | 4/2012 | | |
| WO | WO-2016183501 A1 * | 11/2016 | ........... C07K 14/245 |

OTHER PUBLICATIONS

Karam et al, Vaccine, 2013, 31:1210-1216. available online: Jan. 7, 2013 (Year: 2013).*

(Continued)

*Primary Examiner* — Nita M. Minnifield
(74) *Attorney, Agent, or Firm* — Karen S. Canady; canady + lortz LLP

(57) ABSTRACT

Methods and antibody compositions that displace mannose from the binding pocket of fimbrial adhesin FimH of enterobacteria, including uropathogenic *E. coli*, *Klebsiella oxytoca*, or *Klebsiella pneumoniae*, can be used to disrupt or prevent the attachment of a single layer of bacteria to a mannose-coated surface, or to disrupt or prevent the formation of a multilayer biofilm. The antibody compositions of the invention can thus be used in methods to inhibit, prevent, or reverse the colonization of a surface with enterobacteria that express the bacterial Type 1 fimbrial adhesin FimH, to inhibit or prevent infection of a cell by enterobacteria that express the bacterial Type 1 fimbrial adhesin FimH, such as, for example, uropathogenic *E. coli*, to treat a bacterial infection in subject in need thereof and to treat or prevent inflammatory bowel disease (IBD), among other uses.

20 Claims, 13 Drawing Sheets
Specification includes a Sequence Listing.

(56) References Cited

U.S. PATENT DOCUMENTS

2017/0340718 A1* 11/2017 Kowarik ............... C07K 14/21
2018/0193457 A1* 7/2018 Sokurenko ........... C07K 14/245
2019/0030159 A1* 1/2019 Eldridge ................ A61K 39/39

OTHER PUBLICATIONS

Tchesnokova et al, Infection and Immunity, Oct. 2011, 79/10:3895-3904 (Year: 2011).*
Verdonck et al, Journal of Immunological Methods, 2004, 294:81-88. Available online: Sep. 15, 2004 (Year: 2004).*
Rodreguez et al, JBC, Aug. 16, 2013, 288/33:24125-24139 (Year: 2013).*
Shin et al, FEMS Microbiology Letters, 2010, 303:156-162. Final version published online: Jan. 8, 2010. (Year: 2010).*
Swinney DC (2004) Biochemical mechanisms of drug action: what does it take for success? Nat Rev Drug Discov 3:801-808.
Christopoulos A (2002) Allosteric binding sites on cell-surface receptors: novel targets for drug discovery. Nat Rev Drug Discov 1: 198-210.
Swinney DC (2006) Biochemical mechanisms of New Molecular Entities (NMEs) approved by United States FDA during 2001-2004: mechanisms leading to optimal efficacy and safety. Curr Top Med Chem 6: 461-478.
Jones CH, Pinkner JS, Roth R, Heuser J, Nicholes AV, et al. (1995) FimH adhesin of type 1 pili is assembled into a Fibrillar tip structure in the Enterobacteriaceae. Proc Natl Acad Sci U S A 92: 2081-2085.
Chen SL, Hung CS, Pinkner JS, Walker JN, Cusumano CK, et al. (2009) Positive selection identities an in vivo role for FimH during urinary tract infection in addition to mannose binding. Proc Natl Acad Sci U S A 106: 22439-22444.
Connell I, Agace W, Klemm P, Schembri M, Märild S, et al. (1996) Type 1 fimbrial expression enhances *Escherichia coli* virulence for the urinary tract. Proc Natl Acad Sci U S A 93: 9827-9832.
Krogfelt KA, Bergmans H, Klemm P (1990) Direct evidence that the FimH protein is the mannose-specific adhesin of *Escherichia coli* type 1 fimbriae. Infect Immun 58: 1995-1998.
Martinez JJ, Mulvey MA, Schilling JD, Pinkner JS, Hultgren SJ (2000) Type 1 pilus-mediated bacterial invasion of bladder epithelial cells. Embo J 19: 2803-2812.
Kisielius PV, Schwan WR, Amundsen SK, Duncan JL, Schaeffer AJ (1989) In vivo expression and variation of *Escherichia coli* type 1 and P pili in the urine of adults with acute urinary tract infections. Infect Immun 57: 1656-1662.
Choudhury D, Thompson A, Stojanoff V, Langermann S, Pinkner J, et al. (1999) X-ray structure of the FimC-FimH chaperone-adhesin complex from uropathogenic *Escherichia coli*. Science 285: 1061-1066.
LE Trong I, Aprikian P, Kidd BA, Forero-Shelton M, Tchesnokova V, et al. (2010) Structural basis for mechanical force regulation of the adhesin FimH via finger trap-like sheet twisting. Cell 141: 645-655.
Aprikian P, Tchesnokova V, Kidd B, Yakovenko O, Yarov-Yarovoy V, et al. (2007) Interdomain interaction in the FimH adhesin of *Escherichia coli* regulates the affinity to mannose. J Biol Chem 282: 23437-23446.
Tchesnokova V, Aprikian P, Yakovenko O, Larock C, Kidd B, et al. (2008) Integrin-like allosteric properties of the catch bond-forming FimH adhesin of *Escherichia coli*. J Biol Chem 283: 7823-7833.
Chen W, Lou J, Evans EA, Zhu C (2012) Observing force-regulated conformational changes and ligand dissociation from a single integrin on cells. J Cell Biol 199: 497-512.
Phan UT, Waldron TT, Springer TA (2006) Remodeling of the lectin-EGF-like domain interface in P-and L-selectin increases adhesiveness and shear resistance under hydrodynamic force. Nat Immunol 7: 883-889.
Sooriyaarachchi S, Ubhayasekera W, Park C, Mowbray SL (2010) Conformational changes and ligand recognition of *Escherichia coli* D-xylose binding protein revealed. J Mol Biol 402: 657-668.

Avlani VA, Gregory KJ, Morton CJ, Parker MW, Sexton PM, et al. (2007) Critical role for the second extracellular loop in the binding of both orthosteric and allosteric G protein-coupled receptor ligands. J Biol Chem 282: 25677-25686.
Kim YJ, Hofmann KP, Ernst OP, Scheerer P, Choe HW, et al. (2013) Crystal structure of preactivated arrestin p44. Nature 497: 142-146.
MA Q, Akhter Y, Wilmanns M, Ehebauer MT (2014) Active site conformational changes upon reaction intermediate biotinyl-5'-AMP binding in biotin protein ligase from *Mycobacterium tuberculosis*. Protein Sci 23: 932-939.
Melcher K, Ng LM, Zhou XE, Soon FF, Xu Y, et al. (2009) A gate-latch-lock mechanism for hormone signalling by abscisic acid receptors. Nature 462: 602-608.
Wagner DA, Czajkowski C (2001) Structure and dynamics of the GABA binding pocket: A narrowing cleft that constricts during activation. J Neurosci 21: 67-74.
Carlson KE, Choi I, Gee A, Katzenellenbogen BS, Katzenellenbogen JA (1997) Altered ligand binding properties and enhanced stability of a constitutively active estrogen receptor: evidence that an open pocket conformation is required for ligand interaction. Biochemistry 36: 14897-14905.
Lebon G, Warne T, Edwards PC, Bennett K, Langmead CJ, et al. (2011) Agonist-bound adenosine A2A receptor structures reveal common features of GPCR activation. Nature 474: 521-525.
Duan X, Hall JA, Nikaido H, Quiocho FA (2001) Crystal structures of the maltodextrin/maltose-binding protein complexed with reduced oligosaccharides: flexibility of tertiary structure and ligand binding. J Mol Biol 306: 1115-1126.
Quiocho FA, Spurlino JC, Rodseth LE (1997) Extensive features of tight oligosaccharide binding revealed in high-resolution structures of the maltodextrin transport/chemosensory receptor. Structure 5: 997-1015.
Spurlino JC, Lu GY, Quiocho FA (1991) The 2.3-A resolution structure of the maltose- or Maltodextrin-binding protein, a primary receptor of bacterial active transport and chemotaxis. J Biol Chem 266: 5202-5219.
Rasmussen SG, Choi HJ, Fung JJ, Pardon E, Casarosa P, et al. (2011) Structure of a nanobody-stabilized active state of the beta(2) adrenoceptor. Nature 469: 175-180.
Csermely P, Palotai R, Nussinov R (2010) Induced fit, conformational selection and independent dynamic segments: an extended view of binding events. Trends Biochem Sci 35: 539-546.
Gianni S, Dogan J, Jemth P (2014) Distinguishing induced fit from conformational selection. Biophys Chem 189: 33-39.
Hatzakis NS (2014) Single molecule insights on conformational selection and induced fit mechanism. Biophys Chem 186C: 46-54.
Gaastra W, de Graaf FK. Host-specific fimbrial adhesins of noninvasive enterotoxigenic *Escherichia coli* strains. Microbiol Rev. Jun. 1982;46(2):129-61.
Kisiela, DI et al., Conformational Inactivation Induces Immunogenicity of the Receptor-Binding Pocket of a Bacterial Adhesin. Proceedings of the National Academy of Sciences of the U.S.A. Nov. 19, 2013, vol. 110, No. 47, pp. 19089-19094.
Stahlhut, Steen G. et al. Comparative Structure-Function Analysis of Mannose-Specific FimH Adhesins from Klebsiella pneumoniae and *Escherichia coli*. Journal of Bacteriology, Nov. 2009, p. 6592-6601.
Tchesnokova, Veronika, et al. Type 1 Fimbrial Adhesin FimH Elicits an Immune Response That Enhances Cell Adhesion of *Escherichia coli*. Infection and Immunity, Oct. 2011, p. 3895-3904.
International Search Report and Written Opinion for PCT/US16/32495 (WO16183501 Published Nov. 17, 2016).
Silva DA, Bowman GR, Sosa-Peinado A, Huang X (2011) A role for both conformational selection and induced fit in ligand binding by the LAO protein. PLoS Comput Biol 7: e1002054.
Dissing J, Rangaard B, Christensen U (1993) Activity modulation of the fast and slow isozymes of human cytosolic low-molecular-weight acid phosphatase (ACP1) by purines. Biochim Biophys Acta 1162: 275-282.
Kisiela Di, Rodriguez VB, Tchesnokova V, Avagyan H, Aprikian P, et al. (2013) Conformational inactivation induces immunogenicity of the receptor-binding pocket of a bacterial adhesin. Proc Natl Acad Sci U S A 110: 19089-19094.

(56) References Cited

OTHER PUBLICATIONS

Brochet X, Lefranc MP, Giudicelli V (2008) IMGT/V-QUEST: the highly customized and integrated system for IG and TR standardized V-J and V-D-J sequence analysis. Nucleic Acids Res 36: W503-508.
Giudicelli V, Brochet X, Lefranc MP (2011) IMGT/V-QUEST: IMGT standardized analysis of the immunoglobulin (IG) and T cell receptor (TR) nucleotide sequences. Cold Spring Harb Protoc 2011: 695-715.
Ehlert FJ (1988) Estimation of the affinities of allosteric ligands using radioligand binding and pharmacological null methods. Mol Pharmacol 33: 187-194.
Kenakin T (2004) Allosteric modulators: the new generation of receptor antagonist. Mol Interv 4: 222-229.
Hung CS, Bouckaert J, Hung D, Pinkner J, Widberg C, et al. (2002) Structural basis of tropism of *Escherichia coli* to the bladder during urinary tract infection. Mol Microbiol 44: 903-915.
Nilsson LM, Thomas WE, Trintchina E, Vogel V, Sokurenko EV (2006) Catch bond-mediated adhesion without a shear threshold: trimannose versus monomannose interactions with the FimH adhesin of *Escherichia coli*. J Biol Chem 281: 16656-16663.
Nilsson LM, Thomas WE, Sokurenko EV, Vogel V (2008) Beyond induced-fit receptor-ligand interactions: structural changes that can significantly extend bond lifetimes. Structure 16: 1047-1058.
Wu Y, Eigenbrot C, Liang WC, Stawicki S, Shia S, et al. (2007) Structural insight into distinct mechanisms of protease inhibition by antibodies. Proc Natl Acad Sci U S A 104: 19784-19789.
Mukund S, Shang Y, Clarke HJ, Madjidi A, Corn JE, et al. (2013) Inhibitory mechanism of an allosteric antibody targeting the glucagon receptor. J Biol Chem 288: 36168-36178.
Luo BH, Strokovich K, Walz T, Springer TA, Takagi J (2004) Allosteric beta1 integrin antibodies that stabilize the low affinity state by preventing the swing-out of the hybrid domain. J Biol Chem 279: 27466-27471.
Jaakola VP, Griffith MT, Hanson MA, Cherezov V, Chien EY, et al. (2008) The 2.6 angstrom crystal structure of a human A2A adenosine receptor bound to an antagonist. Science 322: 1211-1217.
Boehr DD, Nussinov R, Wright PE (2009) The role of dynamic conformational ensembles in biomolecular recognition. Nat Chem Biol 5: 789-796.
Seo MH, Park J, Kim E, Hohng S, Kim HS (2014) Protein conformational dynamics dictate the binding affinity for a ligand. Nat Commun 5: 3724.
Henzler-Wildman K, Kern D (2007) Dynamic personalities of proteins. Nature 450: 964-972.
Goh CS, Milburn D, Gerstein M (2004) Conformational changes associated with protein-protein interactions. Curr Opin Struct Biol 14: 104-109.
Wolf-Watz M, Thai V, Henzler-Wildman K, Hadjipavlou G, Eisenmesser EZ, et al. (2004) Linkage between dynamics and catalysis in a thermophilic-mesophilic enzyme pair. Nat Struct Mol Biol 11: 945-949.
Warne T, Moukhametzianov R, Baker JG, Nehmé R, Edwards PC, et al. (2011) The structural basis for agonist and partial agonist action on a β1-adrenergic receptor. Nature 469: 241-244.
Kim E, Lee S, Jeon A, Choi JM, Lee HS, et al. (2013) A single-molecule dissection of ligand binding to a protein with Intrinsic dynamics. Nat Chem Biol 9: 313-318.

Tang C, Schwieters CD, Clore GM (2007) Open-to-closed transition in apo maltose-binding protein observed by paramagnetic NMR. Nature 449: 1078-1082.
Hino T, Arakawa T, Iwanari H, Yurugi-Kobayashi T, Ikeda-Suno C, et al. (2012) G-protein-coupled receptor inactivation by an allosteric inverse-agonist antibody. Nature 482: 237-240.
Doern A, Cao X, Sereno A, Reyes CL, Altshuler A, et al. (2009) Characterization of inhibitory anti-insulin-like growth factor receptor antibodies with different epitope specificity and ligand-blocking properties: implications for mechanism of action in vivo. J Biol Chem 284: 10254-10267.
Nilsson LM, Thomas WE, Sokurenko EV, Vogel V (2006) Elevated shear stress protects *Escherichia coli* cells adhering to surfaces via catch bonds from detachment by soluble inhibitors. Appl Environ Microbiol 72: 3005-3010.
Ding AM, Palmer RJ, Jr., Cisar JO, Kolenbrander PE (2010) Shear-enhanced oral microbial adhesion. Appl Environ Microbiol 76: 1294-1297.
Tchesnokova V, McVeigh AL, Kidd B, Yakovenko O, Thomas WE, et al. (2010) Shear-enhanced binding of intestinal colonization factor antigen I of enterotoxigenic *Escherichia coli*. Mol Microbiol 76: 489-502.
George NP, Wei Q, Shin PK, Konstantopoulos K, Ross JM (2006) *Staphylococcus aureus* adhesion via Spa, ClfA, and SdrCDE to immobilized platelets demonstrates shear-dependent behavior. Arterioscler Thromb Vasc Biol 26: 2394-2400.
Misumi S, Endo M, Mukai R, Tachibana K, Umeda M, et al. (2003) A novel cyclic peptide immunization strategy for preventing HIV-1/AIDS infection and progression. J Biol Chem 278: 32335-32343.
Hoogerhout P, Donders EM, et al. (1995) Conjugates of synthetic cyclic peptides elicit bactericidal antibodies against a conformational epitope on a class 1 outer membrane protein of Neisseria meningitidis. Infect Immun 63: 3473-3478.
Liu Y, El-Achkar TM, Wu XR (2012) Tamm-Horsfall protein regulates circulating and renal cytokines by affecting glomerular filtration rate and acting as a urinary cytokine trap. J Biol Chem 287: 16365-16378.
Myszka DG (1999) Improving biosensor analysis. J Mol Recognit 12: 279-284.
Brooks BR, Brooks CL, 3rd, Mackerell AD, Jr., Nilsson L, Petrella RJ, et al. (2009) CHARMM: the biomolecular simulation program. J Comput Chem 30: 1545-1614.
Mackerell AD, Bashford D, Bellott M, Dunbrack RL, Evanseck JD, et al. (1998) All-atom empirical potential for molecular modeling and dynamics studies of proteins. J Phys Chem B 102: 3586-3616.
Bouckaert J, Berglund J, Schembri M, De Genst E, Cools L, et al. (2005) Receptor binding studies disclose a novel class of high-affinity inhibitors of the *Escherichia coli* FimH adhesin. Mol Microbiol 55: 441-455.
Wellens A, Garofalo C, Nguyen H, Van Gerven N, Slättegård R, et al. (2008) Intervening with urinary tract infections using anti-adhesives based on the crystal structure of the FimHoligomannose-3 complex. PLoS One 3: e2040.
Dagmara I. Kisiela1, et al. (2015) "Inhibition and Reversal of Microbial Attachment by an Antibody with Parasteric Activity against the FimH Adhesin of Uropathogenic *E. coli*" PLoS Pathogens 11(5): e1004857.

* cited by examiner

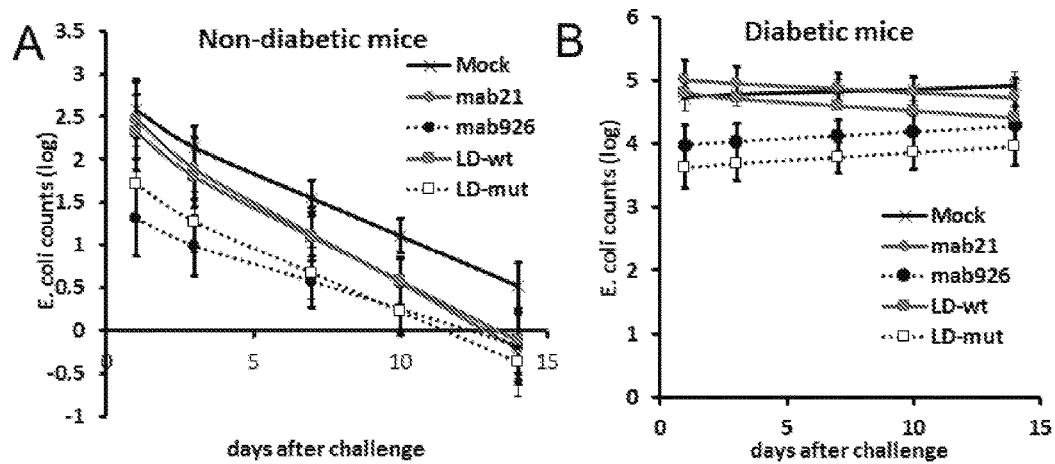

| | day 0 | | | | day 3 | | | |
|---|---|---|---|---|---|---|---|---|
| | Counts | SE | P vs mock | P vs other | Counts | SE | P vs mock | P vs other |
| NON-DIABETIC MICE | | | | | | | | |
| Mock | 2.58 | 0.32 | ref | na | 2.14 | 0.25 | ref | na |
| mAb21 | 2.47 | 0.46 | 0.801 | ref | 1.89 | 0.36 | 0.495 | ref |
| mAb926 | 1.31 | 0.48 | 0.009 | 0.018 | 0.99 | 0.38 | 0.003 | 0.019 |
| LD$^{wt}$ | 2.32 | 0.44 | 0.55 | ref | 1.80 | 0.35 | 0.326 | ref |
| LD$^{mut}$ | 1.71 | 0.44 | 0.048 | 0.149 | 1.27 | 0.35 | 0.012 | 0.114 |
| DIABETIC MICE | | | | | | | | |
| Mock | 4.74 | 0.22 | ref | na | 4.78 | 0.19 | ref | na |
| mAb21 | 5.01 | 0.30 | 0.367 | ref | 4.95 | 0.27 | 0.508 | ref |
| mAb926 | 3.98 | 0.31 | 0.013 | 0.001 | 4.04 | 0.27 | 0.006 | 0.001 |
| LD$^{wt}$ | 4.80 | 0.31 | 0.851 | ref | 4.71 | 0.27 | 0.816 | ref |
| LD$^{mut}$ | 3.62 | 0.31 | <.001 | <.001 | 3.69 | 0.27 | <.001 | <.001 |

| | day 7 | | | | day 10 | | | | day 14 | | | |
|---|---|---|---|---|---|---|---|---|---|---|---|---|
| | Counts | SE | P vs mock | P vs other | Counts | SE | P vs mock | P vs other | Counts | SE | P vs mock | P vs other |
| NON-DIABETIC MICE | | | | | | | | | | | | |
| Mock | 1.55 | 0.20 | ref | na | 1.11 | 0.21 | ref | na | 0.52 | 0.28 | ref | na |
| mAb21 | 1.13 | 0.29 | 0.146 | ref | 0.56 | 0.31 | 0.071 | ref | -0.21 | 0.41 | 0.075 | ref |
| mAb926 | 0.57 | 0.31 | 0.001 | 0.066 | 0.25 | 0.31 | 0.006 | 0.335 | -0.18 | 0.41 | 0.089 | 0.944 |
| LD$^{wt}$ | 1.10 | 0.28 | 0.11 | ref | 0.58 | 0.29 | 0.07 | ref | -0.12 | 0.38 | 0.094 | ref |
| LD$^{mut}$ | 0.67 | 0.28 | 0.002 | 0.12 | 0.22 | 0.30 | 0.003 | 0.226 | -0.37 | 0.39 | 0.023 | 0.512 |
| DIABETIC MICE | | | | | | | | | | | | |
| Mock | 4.83 | 0.18 | ref | na | 4.86 | 0.18 | ref | na | 4.92 | 0.22 | ref | na |
| mAb21 | 4.87 | 0.25 | 0.85 | ref | 4.81 | 0.25 | 0.841 | ref | 4.73 | 0.30 | 0.541 | ref |
| mAb926 | 4.13 | 0.25 | 0.005 | 0.002 | 4.19 | 0.26 | 0.009 | 0.014 | 4.28 | 0.31 | 0.037 | 0.125 |
| LD$^{wt}$ | 4.60 | 0.25 | 0.367 | ref | 4.52 | 0.26 | 0.182 | ref | 4.41 | 0.30 | 0.095 | ref |
| LD$^{mut}$ | 3.79 | 0.25 | <.001 | 0.001 | 3.87 | 0.26 | <.001 | 0.012 | 3.97 | 0.30 | 0.002 | 0.141 |

FIGURE 8

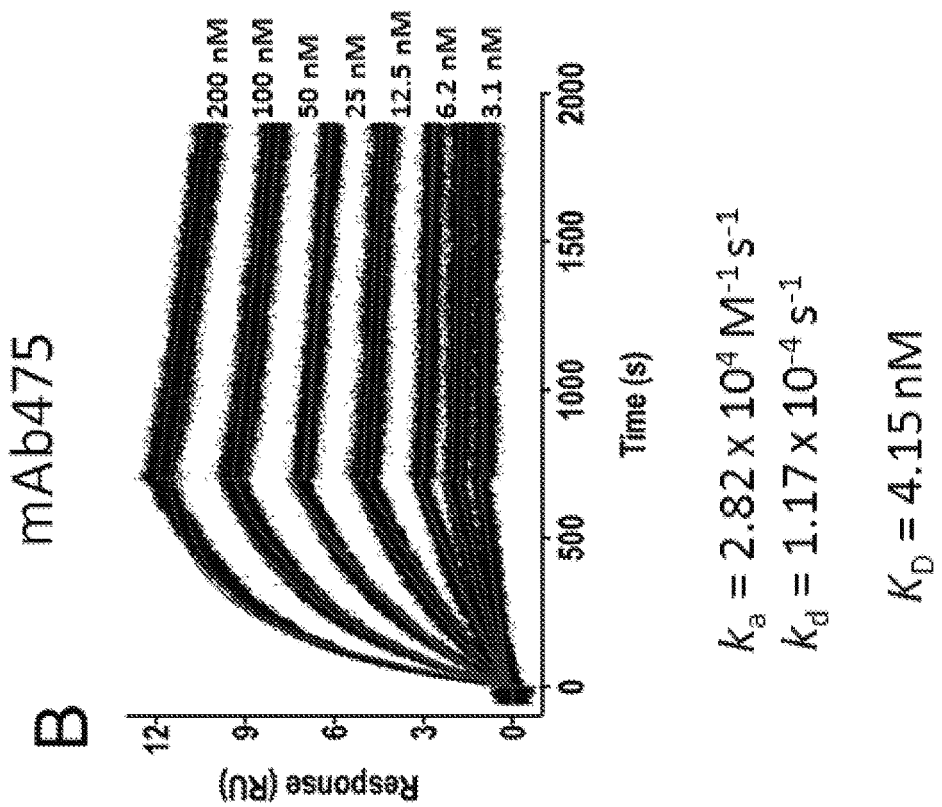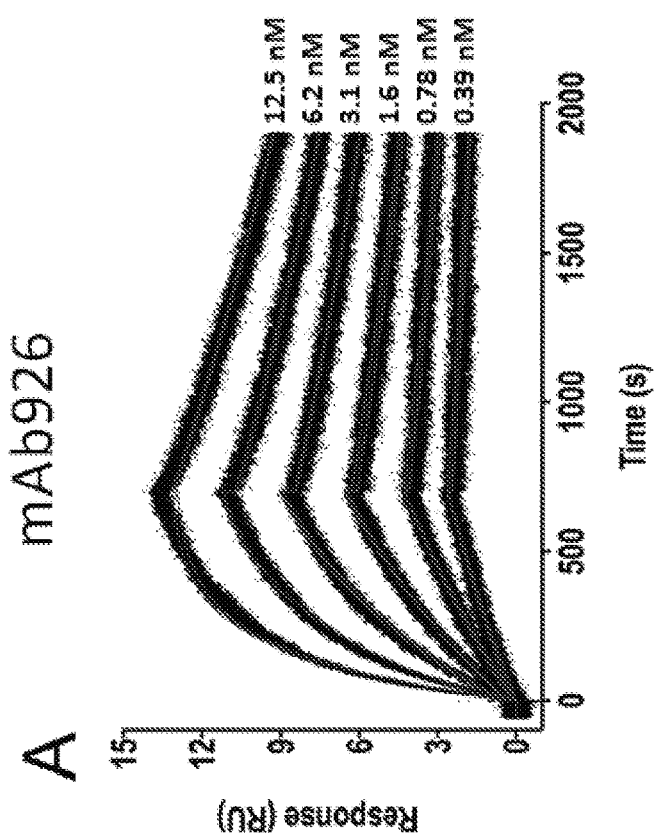
FIGURE 14

|  | | Inactive | | | | | |
|---|---|---|---|---|---|---|---|
| FimH AA | Phe1 | Asn46 | Asp47 | Asp54 | Gln133 | Asn135 | Asp140 |
| Phe1 | 0 | 5.6 | 4.4 | 4.3 (5.5) | 4.8 | 10.4 | 15 |
| Asn46 | 5.5 | 0 | 3 | 3.6 (5.5) | 7.4 | 10.5 | 15.7 |
| Asp47 | 3.8 | 2.9 | 0 | 5.1 (7.1) | 8.1 | 12.4 | 17.3 |
| Asp54 | 4.4 (5.3) | 3.4 (4.9) | 4.4 (6.1) | 0 | 2.9 (4) | 5.7 (7.8) | 11.4 (13.5) |
| Gln133 | 5.4 | 7.8 | 8 | 3.5 (4.8) | 0 | 6.4 | 11.3 |
| Asn135 | 7.6 | 8.2 | 9.3 | 4.5 (6.5) | 4.3 | 0 | 6.3 |
| Asp140 | 7.3 | 10.1 | 10 | 7 (8.5) | 5.3 | 4 | 0 |

(left label: ACTIVE)

```
                         SEQUENCE LISTING

<160> NUMBER OF SEQ ID NOS: 19

<210> SEQ ID NO 1
<211> LENGTH: 106
<212> TYPE: PRT
<213> ORGANISM: Mus musculus

<400> SEQUENCE: 1

Asp Ile Val Met Thr Gln Ser Pro Lys Phe Met Ser Thr Ser Val Gly
1               5                   10                  15

Asp Arg Val Ser Val Thr Cys Lys Ala Ser Gln Asn Val Ser Asn Val
            20                  25                  30

Ala Trp Tyr Gln Gln Lys Pro Gly Gln Ser Pro Lys Ala Met Ile Tyr
        35                  40                  45

Ser Ala Ser Tyr Arg Tyr Ser Gly Val Pro Gly Arg Phe Thr Gly Ser
    50                  55                  60

Gly Ser Gly Thr Asp Phe Thr Leu Thr Ile Asn Asn Val Gln Ser Glu
65                  70                  75                  80

Asp Leu Ala Thr Tyr Phe Cys Gln Gln Asn Ser Ser Phe Pro Phe Thr
                85                  90                  95

Phe Gly Gly Gly Thr Lys Leu Glu Ile Lys
            100                 105

<210> SEQ ID NO 2
<211> LENGTH: 118
<212> TYPE: PRT
<213> ORGANISM: Mus musculus

<400> SEQUENCE: 2

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Tyr Pro Arg Asp Gly Asp Thr Asn Tyr Asn Gly Lys Phe
```

```
                    50                  55                  60
Met Asp Lys Val Thr Leu Thr Ala Asp Lys Ser Ser Asn Thr Ala Tyr
 65                  70                  75                  80

Met Gln Leu Ser Ser Leu Thr Ser Glu Asp Ser Ala Val Tyr Phe Cys
                     85                  90                  95

Glu Val Gly Arg Gly Phe Tyr Gly Met Asp Tyr Trp Gly Gln Gly Thr
                100                 105                 110

Ser Val Thr Val Ser Ser
                115

<210> SEQ ID NO 3
<211> LENGTH: 112
<212> TYPE: PRT
<213> ORGANISM: Mus musculus

<400> SEQUENCE: 3

Asp Val Leu Met Thr Gln Thr Pro Leu Ser Leu Pro Val Ser Leu Gly
  1               5                  10                  15

Asp Gln Ala Ser Ile Ser Cys Arg Ser Ser Gln Asn Ile Val His Asn
                 20                  25                  30

Asn Gly Asn Thr Tyr Leu Glu Trp Tyr Leu Gln Ser Pro Gly Gln Ser
             35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Phe Thr Phe Gly Ser Gly Thr Lys Leu Glu Ile Lys
                100                 105                 110

<210> SEQ ID NO 4
<211> LENGTH: 115
<212> TYPE: PRT
<213> ORGANISM: Mus musculus

<400> SEQUENCE: 4

Gln Val Gln Leu Gln Gln Ser Gly Ala Glu Leu Ala Thr Pro Gly Ala
  1               5                  10                  15

Ser Val Lys Met Ser Cys Lys Ala Ser Gly Tyr Thr Ser Thr Asn Tyr
                 20                  25                  30

Trp Ile His Trp Val Lys Gln Arg Pro Gly Gln Gly Leu Glu Trp Ile
             35                  40                  45

Gly Tyr Ile Asn Pro Thr Ser Gly Tyr Thr Glu Tyr Asn Gln Asn Phe
 50                  55                  60

Lys Asp Lys Ala Thr Leu Thr Ala Asp Lys Ser Ser Ser Thr Ala Tyr
 65                  70                  75                  80

Met Gln Leu Thr Ser Leu Thr Ser Glu Asp Ser Ala Val Tyr Tyr Cys
                 85                  90                  95

Ala Arg Gly Val Ile Arg Asp Phe Trp Gly Gln Gly Thr Thr Leu Thr
                100                 105                 110

Val Ser Ser
        115

<210> SEQ ID NO 5
<211> LENGTH: 106
<212> TYPE: PRT
```

```
<213> ORGANISM: Mus musculus

<400> SEQUENCE: 5

Glu Leu Gln Met Thr Gln Ser Pro Lys Phe Met Ser Thr Ser Val Gly
1               5                   10                  15

Asp Arg Val Ser Val Thr Cys Lys Ala Ser Gln Asn Val Ser Asn Val
            20                  25                  30

Ala Trp Tyr Gln Gln Lys Pro Gly Gln Ser Pro Lys Ala Met Ile Tyr
        35                  40                  45

Ser Ala Ser Tyr Arg Tyr Ser Gly Val Pro Gly Arg Phe Thr Gly Ser
    50                  55                  60

Gly Ser Gly Thr Asp Phe Thr Leu Thr Ile Asn Asn Val Gln Ser Glu
65                  70                  75                  80

Asp Leu Ala Thr Tyr Phe Cys Gln Gln Asn Ser Ser Phe Pro Phe Thr
                85                  90                  95

Phe Gly Gly Gly Thr Lys Leu Glu Ile Lys
            100                 105

<210> SEQ ID NO 6
<211> LENGTH: 117
<212> TYPE: PRT
<213> ORGANISM: Mus musculus

<400> SEQUENCE: 6

Val Gln Leu Leu Glu Ser Gly Ala Glu Leu Val Arg Pro Gly Ser Ser
1               5                   10                  15

Val Lys Ile Ser Cys Lys Ala Ser Gly Tyr Ala Phe Ser Ser Tyr Trp
            20                  25                  30

Met Asn Trp Val Lys Gln Arg Pro Gly Gln Gly Leu Glu Trp Ile Gly
        35                  40                  45

Gln Ile Tyr Pro Arg Asp Gly Asp Thr Asn Tyr Asn Gly Lys Phe Met
    50                  55                  60

Asp Lys Val Thr Leu Thr Ala Asp Lys Ser Ser Asn Thr Ala Tyr Met
65                  70                  75                  80

Gln Leu Ser Ser Leu Thr Ser Glu Asp Ser Ala Val Tyr Phe Cys Glu
                85                  90                  95

Val Gly Arg Gly Phe Tyr Gly Met Asp Tyr Trp Gly Gln Gly Thr Ser
            100                 105                 110

Val Thr Val Ser Ser
            115

<210> SEQ ID NO 7
<211> LENGTH: 112
<212> TYPE: PRT
<213> ORGANISM: Mus musculus

<400> SEQUENCE: 7

Glu Leu Val Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Asn
            20                  25                  30

Asn Gly Asn Thr Tyr Leu Glu Trp Tyr Leu Gln Ser Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80
```

Ser Arg Val Glu Ala Glu Asp Leu Gly Val Tyr Tyr Cys Phe Gln Gly
            85                  90                  95

Ser His Val Pro Phe Thr Phe Gly Gly Thr Lys Leu Glu Ile Lys
            100                 105                 110

<210> SEQ ID NO 8
<211> LENGTH: 114
<212> TYPE: PRT
<213> ORGANISM: Mus musculus

<400> SEQUENCE: 8

Val Gln Leu Leu Glu Ser Gly Ala Glu Leu Ala Thr Pro Gly Ala Ser
1               5                   10                  15

Val Lys Met Ser Cys Lys Ala Ser Gly Tyr Thr Ser Thr Asn Tyr Trp
            20                  25                  30

Ile His Trp Val Lys Gln Arg Pro Gly Gln Gly Leu Glu Trp Ile Gly
        35                  40                  45

Tyr Ile Asn Pro Thr Ser Gly Tyr Thr Glu Tyr Asn Gln Asn Phe Lys
    50                  55                  60

Asp Lys Ala Thr Leu Thr Ala Asp Lys Ser Ser Ser Thr Ala Tyr Met
65                  70                  75                  80

Gln Leu Thr Ser Leu Thr Ser Glu Asp Ser Ala Val Tyr Tyr Cys Ala
                85                  90                  95

Arg Gly Val Ile Arg Asp Phe Trp Gly Gln Gly Thr Thr Leu Thr Val
            100                 105                 110

Ser Ser

<210> SEQ ID NO 9
<211> LENGTH: 32
<212> TYPE: DNA
<213> ORGANISM: Artificial Sequence
<220> FEATURE:
<223> OTHER INFORMATION: Forward primer VL4 for mAb475 light chain

<400> SEQUENCE: 9
ccagttccga gctccagatg acccagtctc ca                                32

<210> SEQ ID NO 10
<211> LENGTH: 32
<212> TYPE: DNA
<213> ORGANISM: Artificial Sequence
<220> FEATURE:
<223> OTHER INFORMATION: Forward primer VL5 for mAb926 light chain

<400> SEQUENCE: 10
ccagatgtga gctcgtgatg acccagactc ca                                32

<210> SEQ ID NO 11
<211> LENGTH: 22
<212> TYPE: DNA
<213> ORGANISM: Artificial Sequence
<220> FEATURE:
<223> OTHER INFORMATION: VH1 primer (mAb475 and mAb926)

<400> SEQUENCE: 11
aggtccagct gctcgagtct gg                                           22

<210> SEQ ID NO 12
<211> LENGTH: 34
<212> TYPE: DNA
<213> ORGANISM: Artificial Sequence
<220> FEATURE:
<223> OTHER INFORMATION: reverse primer for VLr (mAb475 and mAb926)

<400> SEQUENCE: 12
gcgccgtcta gaattaacac tcattcctgt tgaa             34

<210> SEQ ID NO 13
<211> LENGTH: 30
<212> TYPE: DNA
<213> ORGANISM: Artificial Sequence
<220> FEATURE:
<223> OTHER INFORMATION: primer for VH3r (IgG1-specific)

<400> SEQUENCE: 13
aggcttacta gtacaatccc tgggcacaat             30

<210> SEQ ID NO 14
<211> LENGTH: 279
<212> TYPE: PRT
<213> ORGANISM: Escherichia coli

<400> SEQUENCE: 14

Phe Ala Cys Lys Thr Ala Asn Gly Thr Ala Ile Pro Ile Gly Gly
1               5                   10                  15

Ser Ala Asn Val Tyr Val Asn Leu Ala Pro Val Val Asn Val Gly Gln
                20                  25                  30

Asn Leu Val Val Asp Leu Ser Thr Gln Ile Phe Cys His Asn Asp Tyr
            35                  40                  45

Pro Glu Thr Ile Thr Asp Tyr Val Thr Leu Gln Arg Gly Ser Ala Tyr
50                  55                  60

Gly Gly Val Leu Ser Asn Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
130                 135                 140

Val Trp Asn Ile Tyr Ala Asn Asn Asp Val Val Pro Thr Gly Gly
145                 150                 155                 160

Cys Asp Val Ser Ala Arg Asp Val Thr Val Thr Leu Pro Asp Tyr Pro
                165                 170                 175

Gly Ser Val Pro Ile Pro Leu Thr Val Tyr Cys Ala Lys Ser Gln Asn
            180                 185                 190

Leu Gly Tyr Tyr Leu Ser Gly Thr Thr Ala Asp Ala Gly Asn Ser Ile
        195                 200                 205

Phe Thr Asn Thr Ala Ser Phe Ser Pro Ala Gln Gly Val Gly Val Gln
    210                 215                 220

Leu Thr Arg Asn Gly Thr Ile Ile Pro Ala Asn Asn Thr Val Ser Leu
225                 230                 235                 240

Gly Ala Val Gly Thr Ser Ala Val Ser Leu Gly Leu Thr Ala Asn Tyr
                245                 250                 255

Ala Arg Thr Gly Gly Gln Val Thr Ala Gly Asn Val Gln Ser Ile Ile
            260                 265                 270

Gly Val Thr Phe Val Tyr Gln

```
        275

<210> SEQ ID NO 15
<211> LENGTH: 279
<212> TYPE: PRT
<213> ORGANISM: Escherichia coli

<400> SEQUENCE: 15

Phe Ala Cys Lys Thr Ala Asn Gly Thr Ala Ile Pro Ile Gly Gly
1               5                   10                  15

Ser Ala Asn Val Tyr Val Asn Leu Ala Pro Ala Val Asn Val Gly Gln
                20                  25                  30

Asn Leu Val Val Asp Leu Ser Thr Gln Ile Phe Cys His Asn Asp Tyr
            35                  40                  45

Pro Glu Thr Ile Thr Asp Tyr Val Thr Leu Gln Arg Gly Ala Ala Tyr
        50                  55                  60

Gly Gly Val Leu Ser Ser Phe Ser Gly Thr Val Lys Tyr Asn Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
130                 135                 140

Val Trp Asn Ile Tyr Ala Asn Asn Asp Val Val Pro Thr Gly Gly
145                 150                 155                 160

Cys Asp Val Ser Ala Arg Asp Val Thr Val Thr Leu Pro Asp Tyr Pro
                165                 170                 175

Gly Ser Val Pro Ile Pro Leu Thr Val Tyr Cys Ala Lys Ser Gln Asn
            180                 185                 190

Leu Gly Tyr Tyr Leu Ser Gly Thr Thr Ala Asp Ala Gly Asn Ser Ile
        195                 200                 205

Phe Thr Asn Thr Ala Ser Phe Ser Pro Ala Gln Gly Val Gly Val Gln
210                 215                 220

Leu Thr Arg Asn Gly Thr Ile Ile Pro Ala Asn Asn Thr Val Ser Leu
225                 230                 235                 240

Gly Ala Val Gly Thr Ser Ala Val Ser Leu Gly Leu Thr Ala Asn Tyr
                245                 250                 255

Ala Arg Thr Gly Gly Gln Val Thr Ala Gly Asn Val Gln Ser Ile Ile
            260                 265                 270

Gly Val Thr Phe Val Tyr Gln
        275

<210> SEQ ID NO 16
<211> LENGTH: 11
<212> TYPE: PRT
<213> ORGANISM: Mus musculus

<400> SEQUENCE: 16

Cys Gln Gln Asn Ser Ser Phe Pro Phe Thr Phe
1               5                   10

<210> SEQ ID NO 17
<211> LENGTH: 11
<212> TYPE: PRT
```

```
<213> ORGANISM: Mus musculus

<400> SEQUENCE: 17

Cys Phe Gln Gly Ser His Val Pro Phe Thr Phe
1               5                   10

<210> SEQ ID NO 18
<211> LENGTH: 13
<212> TYPE: PRT
<213> ORGANISM: Mus musculus

<400> SEQUENCE: 18

Cys Glu Val Gly Arg Gly Phe Tyr Gly Met Asp Tyr Trp
1               5                   10

<210> SEQ ID NO 19
<211> LENGTH: 10
<212> TYPE: PRT
<213> ORGANISM: Mus musculus

<400> SEQUENCE: 19

Cys Ala Arg Gly Val Ile Arg Asp Phe Trp
1               5                   10
```

COMPOSITIONS AND METHODS FOR TREATMENT AND PREVENTION OF UROPATHOGENIC *E. COLI* INFECTION

This application claims benefit of United States provisional patent application Nos. 62/160,852, filed May 13, 2015, and 62/208,913, filed Aug. 24, 2015, and the entire contents of each are incorporated by reference into this application.

ACKNOWLEDGEMENT OF GOVERNMENT SUPPORT

This invention was made with government support under Grant No. R21 AI103846, awarded by the National Institutes of Health. The government has certain rights in the invention.

REFERENCE TO A SEQUENCE LISTING SUBMITTED VIA EFS-WEB

The content of the ASCII text file of the sequence listing named "UW59WOU2_SL", which is 15 kb in size, was created on May 12, 2016, and electronically submitted via EFS-Web herewith the application. The sequence listing is incorporated herein by reference in its entirety.

TECHNICAL FIELD OF THE INVENTION

This invention relates to methods and antibody compositions that displace mannose from the binding pocket of fimbrial adhesin FimH of enterobacteria, including uropathogenic *E. coli, Klebsiella oxytoca,* or *Klebsiella pneumoniae*. The methods and antibody compositions can be used to disrupt or prevent the attachment of a single layer of bacteria to a mannose-coated surface, or to disrupt or prevent the formation of a multilayer biofilm. The antibody compositions of the invention can thus be used in methods to inhibit, prevent, or reverse the colonization of a surface with enterobacteria that express the bacterial Type 1 fimbrial adhesin FimH, to inhibit or prevent infection of a cell by enterobacteria that express the bacterial Type 1 fimbrial adhesin FimH, such as, for example, uropathogenic *E. coli*, to treat a bacterial infection in subject in need thereof, and to treat or prevent inflammatory bowel disease (IBD), among other uses.

BACKGROUND OF THE INVENTION

Receptor-ligand interactions are among the most basic biological phenomena involved in cell signaling, adhesion and pathogen attachment. Antibody- or small molecule-based inhibitors of these interactions are of great importance for various preventive and therapeutic implications, including development of protective vaccines. Two general types of inhibitory mechanisms have been described to date. Orthosteric inhibitors directly compete with ligands for the binding pocket and, thus, their receptor-inhibitory activity is of a competitive nature (Swinney 2004). In contrast, allosteric inhibitors exert their effects via interaction with a site that is separate from the ligand-binding pocket and accomplish the inhibition in a non-competitive manner (Christopoulos 2002). Non-competitive inhibition is less sensitive to endogenous ligand and thus is generally more effective pharmacologically (Swinney 2006).

FimH is a 30 kDa lectin-like protein that is incorporated into the tip of surface hair-like structures of *E. coli* and other enterobacteria called type 1 fimbriae (Jones, et al. 1995). It exhibits specificity to glycoproteins carrying terminally exposed mannose and is critical for the virulence of uropathogenic strains of *E. coli* (Chen, et al. 2009; Connell, et al. 1996; Kisielius, et al. 1989; Krogfelt, et al. 1990; Martinez, et al. 2000). FimH has two domains: the C-terminal pilin domain that anchors the adhesin to the fimbrial rod and the N-terminal lectin domain that is responsible for mannose binding (Choudhury, et al. 1999). The binding pocket in the lectin domain shifts between open and tightened conformations with low ($K_D$=298 µM)- and high ($K_D$=1.2 µM)—affinity for mannose, respectively (Aprikian, et al. 2007; Le Trong, et al. 2010; Tchesnokova, et al. 2008). The low-affinity (inactive) state of the lectin domain is allosterically stabilized by its interaction with the pilin domain that sustains a finger-trap-like twist in the β-sheets of the binding domain (Le Trong, et al. 2010). The high-affinity (active) state is induced by ligand binding and/or separation of the domains, with the latter facilitated by force during bacterial adhesion under flow conditions. FimH-like force-activated adhesion has been described in several other adhesive systems of different bacterial species as well as eukaryotic cells. For example, proteins like integrins (Chen, et al. 2012) or P/L-selectins (Phan, et al. 2006) exhibit a shift between inactive and active conformations under shear force.

The existence of two alternative conformations of the mannose-binding pocket of FimH reflects a broad phenomenon in the biology of receptor-ligand interactions, including enzyme binding to substrates and products. In fact, the century-old static 'lock-and-key' model of the interaction mechanism is considered now to be too rigid for many if not the majority of receptor proteins and enzymes. It has been shown that ligand-binding pockets are typically composed of residues on flexible loops and dynamically shift between active and inactive conformations, with relatively high and low (often unmeasurable) affinity for the ligand, respectively (Avlani, et al. 2007; Kim, et al. 2013; Ma, et al. 2014; Melcher, et al. 2009; Sooriyaarachchi, et al. 2010). Generally, the ligand-bound active pocket assumes a more contracted shape than the ligand-free inactive pocket, so the corresponding receptor conformers are commonly referred to as open versus closed (or tightened) states (Carlson, et al. 1997; Lebon, et al. 2011; Melcher, et al. 2009; Wagner and Czajkowski 2001). Some well-studied examples of receptors with such pocket dynamics include allosteric proteins such as maltose-binding protein (Duan, et al. 2001; Quiocho, et al. 1997; Spurlino, et al. 1991), and G-protein-coupled receptors (GPCRs) (Lebon, et al. 2011; Rasmussen, et al. 2011; Wagner and Czajkowski 2001).

Two general models have been proposed to describe the effect of ligand on the conformation of receptor binding pockets. In the 'induced fit' model, the active state of the pocket is assumed only after ligand binds to the inactive state, while in the 'conformational selection' model, the inactive and active states coexist in the absence of ligand, but the active state is stabilized by ligand binding (Csermely, et al. 2010; Gianni, et al. 2014; Hatzakis 2014). More complex models of ligand-receptor recognition that combine the two models are also considered (Silva, et al. 2011). All models allow for initial weak interaction of the ligand with the inactive state of binding pocket, and this weak interaction has been repeatedly shown to involve only a subset of the receptor residues that interact with the ligand in the strongly-binding active state (Carlson, et al. 1997; Lebon, et al. 2011; Melcher, et al. 2009; Silva, et al. 2011; Sooriyaarachchi, et al. 2010).

Partial interaction of the ligand with the binding pocket leaves the remaining residues, which only interact with the ligand when the pocket is in the active state, free in theory to bind to an additional compound. Such a compound could potentially act as an inhibitor by interfering with the switch of the pocket into the active state. Such an inhibitor would not fit the accepted definition of either orthosteric inhibitors that cannot bind simultaneously with ligand, or allosteric inhibitors that should bind away from the binding pocket. Instead, because such inhibitors would bind next to the ligand, they could be classified as parasteric inhibitors.

There remains a need for effective means of inhibiting FimH activity in order to disrupt biofilm formation and treat pathogenic infections, as well as prevent infection via contaminated biomedical devices.

SUMMARY OF THE INVENTION

The invention meets these needs and others by providing methods and compositions that inhibit FimH activity with a surprising degree of efficacy. Described herein is a type of inhibitory monoclonal antibody against the mannose-binding adhesin of *E. coli*, FimH, that does not fall into either of the known two categories of inhibitors. Like an allosteric inhibitor, this antibody exerts non-competitive inhibition, but like an orthosteric inhibitor, it binds within the ligand-binding pocket. Unlike the latter, however, it forces the conversion of the binding pocket to an open, inactive conformation, even when the pocket is occupied by the ligand mannose.

In one embodiment, the invention provides a composition comprising an antibody that specifically recognizes and binds uropathogenic *Escherichia coli* (*E. coli*) fimbrial adhesin FimH and is capable of preventing colonization of a surface by uropathogenic *E. coli*. In one embodiment, the antibody comprises a light chain variable region, and, optionally, a heavy chain variable region, or polynucleotide(s) encoding same. In a typical embodiment, the light chain variable region comprises an amino acid sequence selected from the group consisting of SEQ ID NO: 1, SEQ ID NO: 3, and sequences at least 90% identical thereto. The light chain variable region comprises one, two or three of three complementarity determining regions (CDRs), CDR1, CDR2, and CDR3. The CDR1 sequence comprises QNVSN (residues 27-31 of SEQ ID NO: 1) or QNIVHNNGNTY (residues 27-37 of SEQ ID NO: 3). The CDR2 sequence comprises SAS (residues 49-51 of SEQ ID NO: 1) or KVS (residues 55-57 of SEQ ID NO: 3). The CDR3 sequence comprises QQNSSFPFT (residues 88-96 of SEQ ID NO: 1) or FQGSHVPFT (residues 94-102 of SEQ ID NO: 3). In a typical embodiment, the heavy chain variable region comprises an amino acid sequence selected from the group consisting of SEQ ID NO: 2, SEQ ID NO: 4, and sequences at least 90% identical thereto. The heavy chain variable region comprises one, two or three of three complementarity determining regions (CDRs), CDR1, CDR2, and CDR3. The CDR1 sequence comprises GYAFSSYW (residues 26-33 of SEQ ID NO: 2) or GYTSTNYW (residues 26-33 of SEQ ID NO: 4). The CDR2 sequence comprises IYPRDGDT (residues 51-58 of SEQ ID NO: 2) or INPTSGYT (residues 51-58 of SEQ ID NO: 4). The CDR3 sequence comprises EVGRGFYGMDY (residues 97-107 of SEQ ID NO: 2) or ARGVIRDF (residues 97-104 of SEQ ID NO: 4). In one embodiment, the light chain variable region comprises CDR1 (QNIVHNNGNTY, residues 27-37 of SEQ ID NO: 3), CDR2 (KVS, residues 55-57 of SEQ ID NO: 3), and CDR3 (FQGSHVPFT, residues 94-102 of SEQ ID NO: 3), and the heavy chain variable region comprises CDR1 (GYTSTNYW, residues 26-33 of SEQ ID NO: 4), CDR2 (INPTSGYT, residues 51-58 of SEQ ID NO: 4), and CDR3 (ARGVIRDF, residues 97-104 of SEQ ID NO: 4).

In some embodiments, the amino acid sequence of the light chain variable region has at least 95% identity with SEQ ID NO: 1 or 3. Representative examples of the amino acid sequence of the light chain variable region include, but are not limited to, the group consisting of: SEQ ID NO: 1, 3, 5, and 7. In some embodiments, the amino acid sequence of the light chain variable region is SEQ ID NO: 3.

In some embodiments, the amino acid sequence of the heavy chain variable region sequence has at least 95% identity with SEQ ID NO: 2 or 4. Representative examples of the amino acid sequence of the heavy chain variable region include, but are not limited to, the group consisting of: SEQ ID NO: 2, 4, 6, and 8. In some embodiments, the amino acid sequence of the heavy chain variable region is SEQ ID NO: 4.

In one embodiment, the antibody binds within the mannose-binding pocket of the uropathogenic *E. coli* FimH. In a typical embodiment, the antibody binds within amino acid residues 133-142 of the FimH amino acid sequence shown in SEQ ID NO: 14. In some embodiments, the antibody binds a conformational epitope selected from I52, N135, N136, Y137, N138, and D140 of SEQ ID NO: 14; and F1, N46, I52, D54, Q133, N135 and N136 of SEQ ID NO: 14. In one embodiment, the antibody inhibits bacterial adhesion with an IC50 less than about 15 nM. In another embodiment, the antibody inhibits bacterial adhesion with an IC50 less than 1 nM. In one particular embodiment, the antibody inhibits bacterial adhesion with an IC50 of about 14 nM. In another particular embodiment, the antibody inhibits bacterial adhesion with an IC50 of about 0.4 nM.

In one particular embodiment, the antibody binds within the mannose-binding pocket of FimH and thereby competes with mannose for binding to FimH. In another particular embodiment, the antibody binds within the mannose-binding pocket of FimH and thereby releases mannose bound to the pocket in a non-competitive manner, for example, by binding to a side of the pocket. In these manners, the antibody can both prevent attachment of bacteria to a mannose-coated surface, and detach bacteria already attached to a mannose-coated surface. The antibody can be used to disrupt or prevent the attachment of a single layer of bacteria to a mannose-coated surface, or to disrupt or prevent the formation of a multilayer biofilm. The invention provides a method of displacing mannose from the binding pocket of fimbrial adhesin FimH of enterobacteria, such as uropathogenic *E. coli*, *Klebsiella oxytoca*, or *Klebsiella pneumoniae*, and other Type 1 fimbriae-expressing bacteria. In a typical embodiment, the method comprises contacting the binding pocket with a composition of the invention.

In some embodiments, the antibody further comprises a heterologous sequence. Examples of a heterologous sequence include, but are not limited to, sequence encoding all or a portion of a polypeptide, antibody, epitope, or other moiety that would not be found adjacent to the recited sequence under natural conditions. Such heterologous moieties can be useful for improving solubility, delivery, immunogenicity, efficacy, detection, or identification of the recited sequence or molecule. In some embodiments, the heterologous sequence is inert or an unrelated sequence. The antibody can be, for example, one or more of a polyclonal antibody, a monoclonal antibody, a humanized antibody, a human antibody, an antibody derivative, a veneered antibody, a diabody, an antibody derivative, a recombinant human antibody, a chimeric antibody, or an antibody fragment. In one embodiment, the antibody is a monoclonal antibody. The invention additionally provides polynucleotides encoding antibodies of the invention. Thus, in some embodiments, the antibody composition of the invention comprises a nucleic acid molecule encoding the recited antibody. In some embodiments, one nucleic acid molecule encodes the entire antibody or functional fragment thereof, while in others, separate nucleic acid molecules are provided that encode portions, regions, and/or fragments of the antibody.

In some embodiments, the composition of the invention further comprises a carrier. The carrier can be a pharmaceutically acceptable carrier, or other carrier that facilitates use of the antibody composition. The invention additionally provides a kit comprising a package or container that is compartmentalized to receive one or more containers such as vials, tubes, and the like, each of the container(s) comprising one of the separate elements (e.g., antibodies, carriers) to be used in the method.

In one embodiment, the invention provides a method to inhibit, prevent, or reverse the colonization of a surface with enterobacteria that express the bacterial Type 1 fimbrial adhesin FimH. Examples of enterobacteria include, but are not limited to, *E. coli, K. pneumoniae, K. oxytoca, Shigella, Serratia spp, Enterobacter spp, Citrobacter*, and *Edwardsiella*. The surface can be a biological or non-biological surface. Examples of biological surfaces that can be colonized by enterobacteria include, but are not limited to, mucosal epithelial surfaces. Examples of non-biological surfaces that can be colonized by enterobacteria include, but are not limited to, catheters and intubation devices. The method typically comprises contacting the surface with a composition comprising an antibody of the invention.

In one embodiment, the invention provides a method to inhibit or prevent infection of a cell by enterobacteria that express the bacterial Type 1 fimbrial adhesin FimH, such as, for example, uropathogenic *E. coli*. The method comprises administering to a tissue infected with the enterobacteria, e.g., uropathogenic *E. coli*, or other species of *E. coli, K. pneumoniae, K. oxytoca, Shigella, Serratia spp, Enterobacter spp, Citrobacter*, and *Edwardsiella*. The method comprises contacting the cell with an effective amount of a composition of the invention, thereby inhibiting or preventing infection of the cell.

In one embodiment, the invention provides a method to treat a bacterial infection in subject in need thereof, wherein the subject is infected with enterobacteria such as *E. coli, K. pneumoniae, K. oxytoca, Shigella, Serratia spp, Enterobacter spp, Citrobacter*, and *Edwardsiella*. In some embodiments, the enterobacteria is uropathogenic *E. coli, Klebsiella oxytoca,* or *Klebsiella pneumoniae*. The method comprises administering to the subject an effective amount of a composition as described herein, thereby treating a bacterial infection in the subject. In some embodiments, the bacterial infection is colitis or sepsis. Additional representative examples of infections to be treated by the method include, but are not limited to, pneumonia, including ventilated pneumonia in intubated patients, catheter-associated infections, including urinary and blood line catheters, newborn meningitis, urinary tract infections, including those resulting from vaginal and periurethral colonization, and wound infections.

In one embodiment, the invention provides a method of treating or preventing inflammatory bowel disease (IBD) in a subject. The method comprises administering to the subject an effective amount of a composition as described herein, thereby treating or preventing IBD in the subject. In one embodiment, the administering is by subcutaneous, topical, transdermal, intravenous, oral, or intracolonic administration.

BRIEF DESCRIPTION OF THE DRAWINGS

FIG. 8. Effect of passive and active immunization on $E.\ coli$ infection in mice.

Estimated mean counts of $E.\ coli$ CFT073 (log 10/10 µl) in urine of different groups of non-diabetic (A) and diabetic (B) mice over 14 days after the challenge. Animals were passively or actively immunized with designated mAbs (150 µg/mouse) or LD antigen (15 µg/mouse), respectively, or immunized with incomplete Freund's adjuvant only (IFA, mock). (C) Statistical significance of the data presented in A and B.

Figure 9:
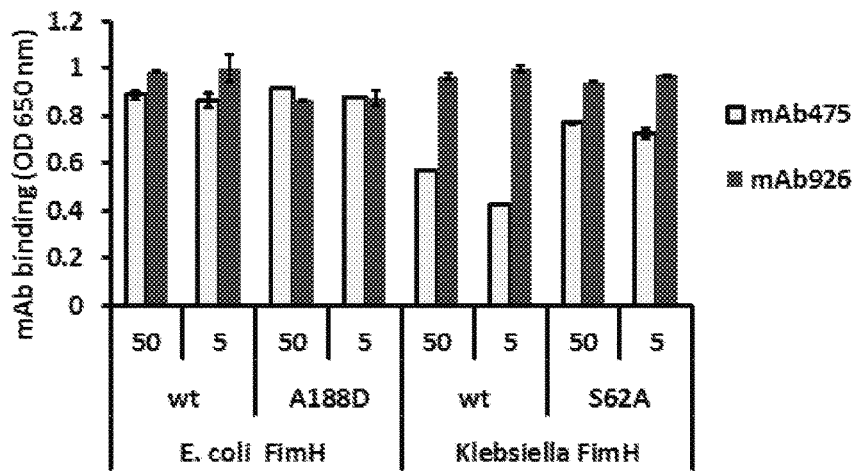

FIG. 9. Recognition of $Klebsiella$ FimH by anti-$E.\ coli$ FimH antibodies. Binding of the mAb475 and mAb926 to $E.\ coli$ and $Klebsiella$ fimbrial FimH. Type 1 fimbriae carrying different FimH variants (FimH$^{wt}$ and FimH$^{S62A}$ mutant) were incubated with different concentrations of mAbs (50 and 5 µg/ml). Data shown are mean±SD of duplicates from one representative experiment.

Figure 10:
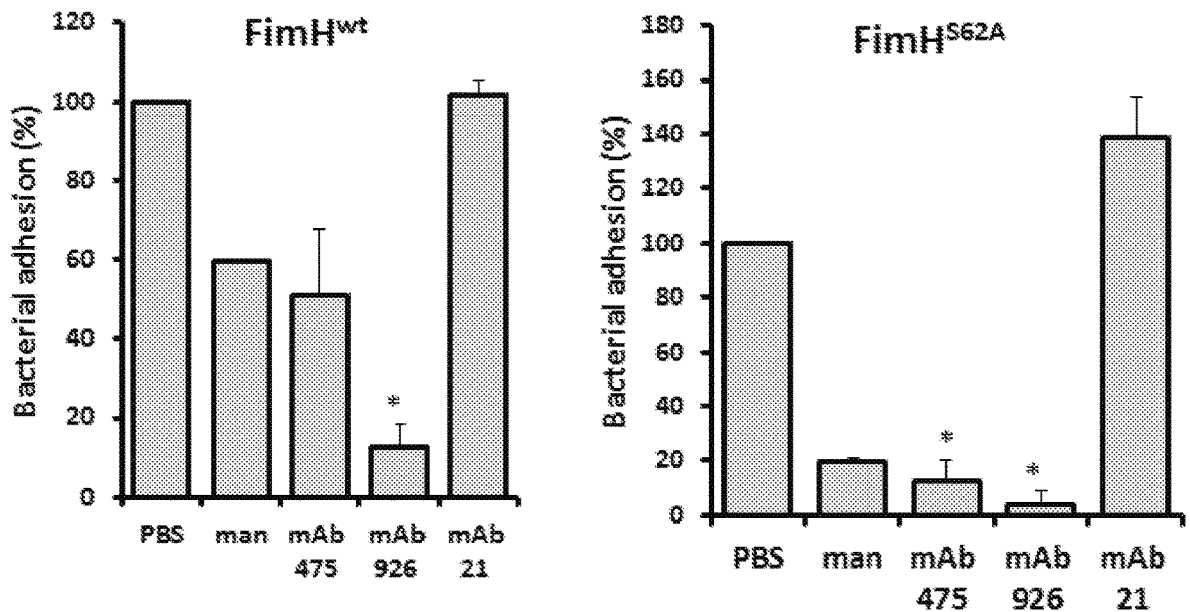

FIG. 10. Inhibitory potency of mAb926 and mAb475. Binding of FimH$^{wt}$- and FimH$^{S62A}$-expressing $Klebsiella\ pneumoniae$ to surface-immobilized RNaseB in the presence of 1% mannose or 50 µg/ml anti-FimH antibodies. Data are mean±SD (n=2 independent experiments).

Figure 11:
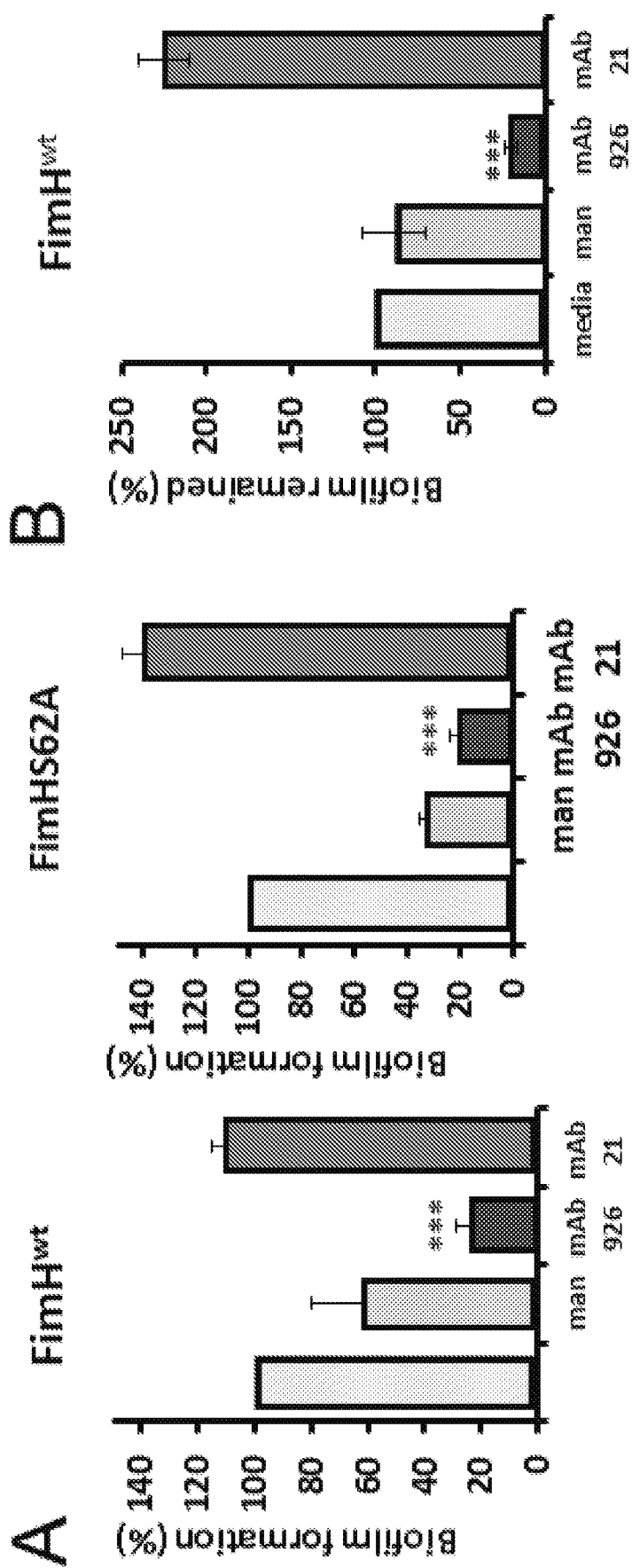

FIG. 11. Effect of mAb926 and mAb475 on biofilm formed by $Klebsiella\ pneumoniae$ on RNaseB-coated surfaces. (A) Biofilm formation by $Klebsiella$ in the presence of 1% mannose or 50 µg/ml monoclonal antibodies. Data (mean±SD, n=3 independent experiments). (B) Detachment of 14 h-old $Klebsiella$ biofilm in the presence of 1% mannose or 50 µg/ml mAbs. Data (mean±SD, n=3 independent experiments). Biofilm was quantified using the crystal violet staining method. *, P≤0.05, **, P≤0.0005 (one sample t-test).

Figure 12:
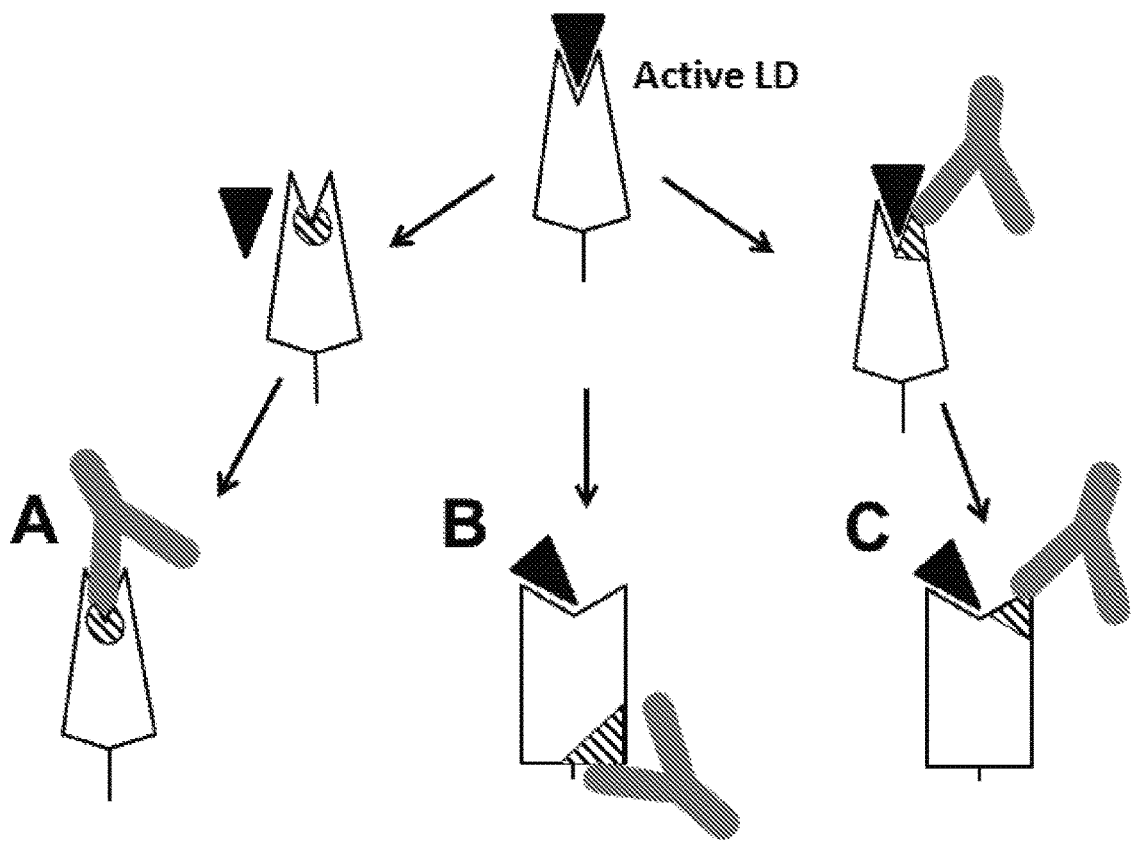

FIG. 12. Schematic representation of different types of antibodies against lectin domain (LD) of FimH. (A) Orthosteric antibody. (B) Allosteric antibody. (C) Parasteric antibody. The triangular indent on the LD represents the mannose-binding site, and the black triangle represents the mannose ligand. The striped elements represent the functional epitopes for orthosteric, allosteric and parasteric antibodies, respectively.

Figure 13:
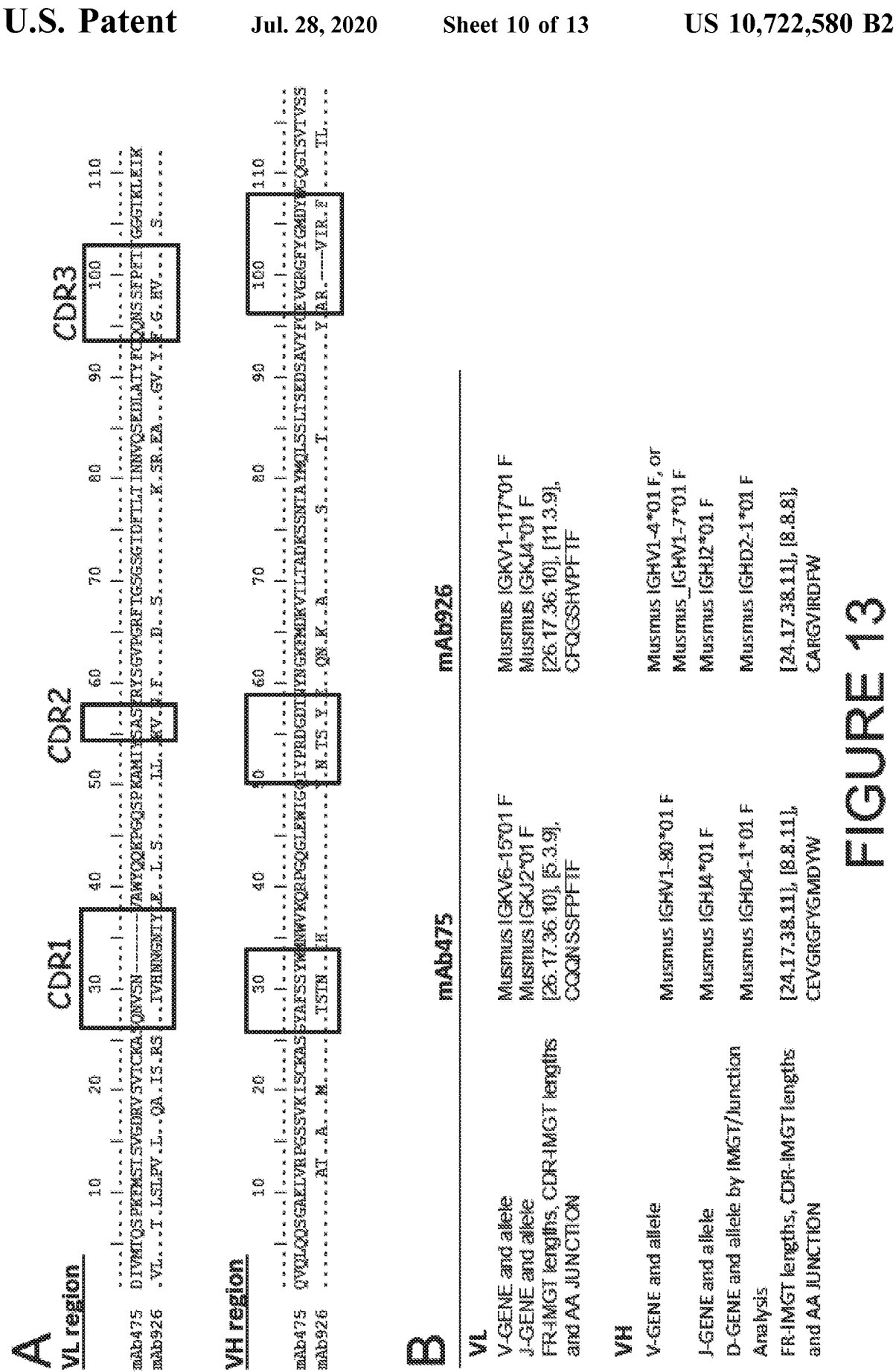

FIG. 13. VH and VL region sequences of mAb475 and mAb926. (A) Alignment of VL (SEQ ID NOs: 1, 3) and VH (SEQ ID NOs: 2, 4) region amino acid sequences of mAb475 (SEQ ID NOs: 1, 2) and mAb926 (SEQ ID NOs: 3, 4). (B) Germline origin of mAb475 and mAb926. Positions of the complementarity determining regions (CDRs, outlined), and germline origins of the mAbs as determined by IMGT/V-Quest software. The first eight amino acids from N-terminus of VL (SEQ ID NOs: 16-17) and VH (SEQ ID NOs: 18-19) regions of the antibodies (mAb475, SEQ ID NOs: 16, 18; mAb926, SEQ ID NOs: 17, 19) overlapped with sequences of forward primers used for the Ig gene amplification and sequencing and thus are shown as in germline origin.

FIG. 14. Surface plasmon resonance measurements of antibody binding to CM5 chip-immobilized fimbriae with FimH$^{wt}$. (A) Binding of mAb926. (B) Binding of mAb475. The experimental data (black curves) were fitted to a 1:1 binding model (grey curves) using BIAevaluation 2.0.4 software (GE Healthcare). Duplicates of each concentration are shown.

Figure 15:
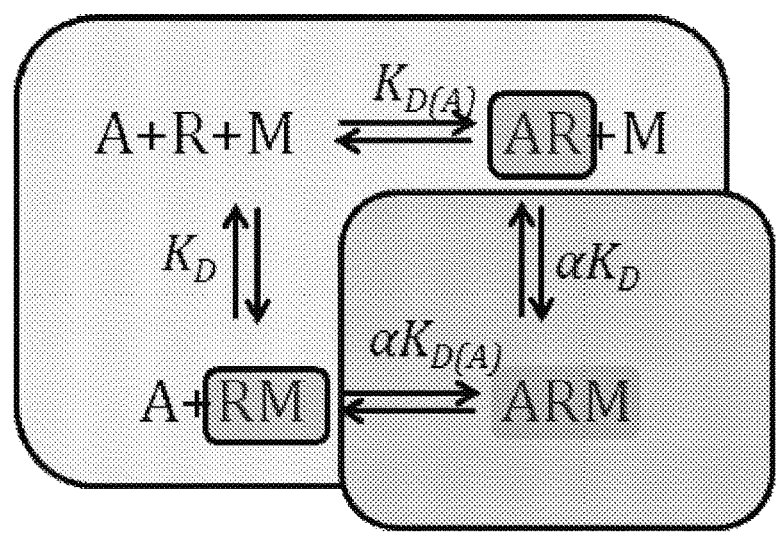

FIG. 15. Model of competitive (light grey field) vs non-competitive (dark grey field) binding of mannose and antibody to FimH receptor. R denotes FimH receptor, A denotes antibody and M denotes mannose. $K_D$ and $K_D$ (A) are respective equilibrium dissociation constants and α denotes the cooperative factor.

Figures 16, 17:
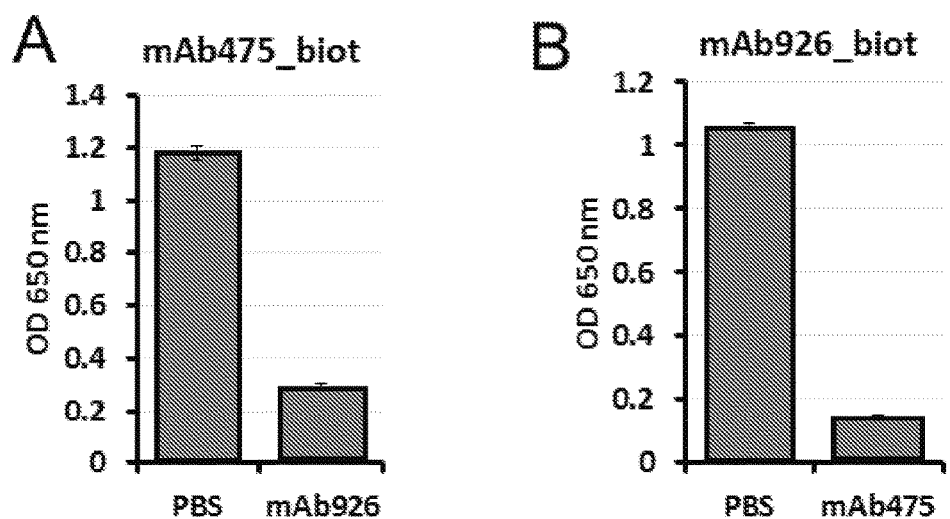

FIG. 16. Inhibitory mAbs interfere with each other's binding to FimH. Binding of biotinylated mAb475 (A) and biotinylated mAb926 (B) to the high affinity variant of FimH (FimH$^{wt:(186-201)FocH}$, (Aprikian, et al. 2007)) pre-incubated with PBS or designated antibody. The data shown are mean±SD of triplicates from one representative experiment of multiple experiments that were performed with similar settings.

FIG. 17. Distances between ligand-contacting residues in the active and the inactive conformations of the FimH binding-pocket. All distances are shown in Å and were measured between the heavy atoms of designated residues in the active-(PDB 1UWF) and the inactive-(PDB 3JWN) conformers of FimH by PyMol.

Figure 18:
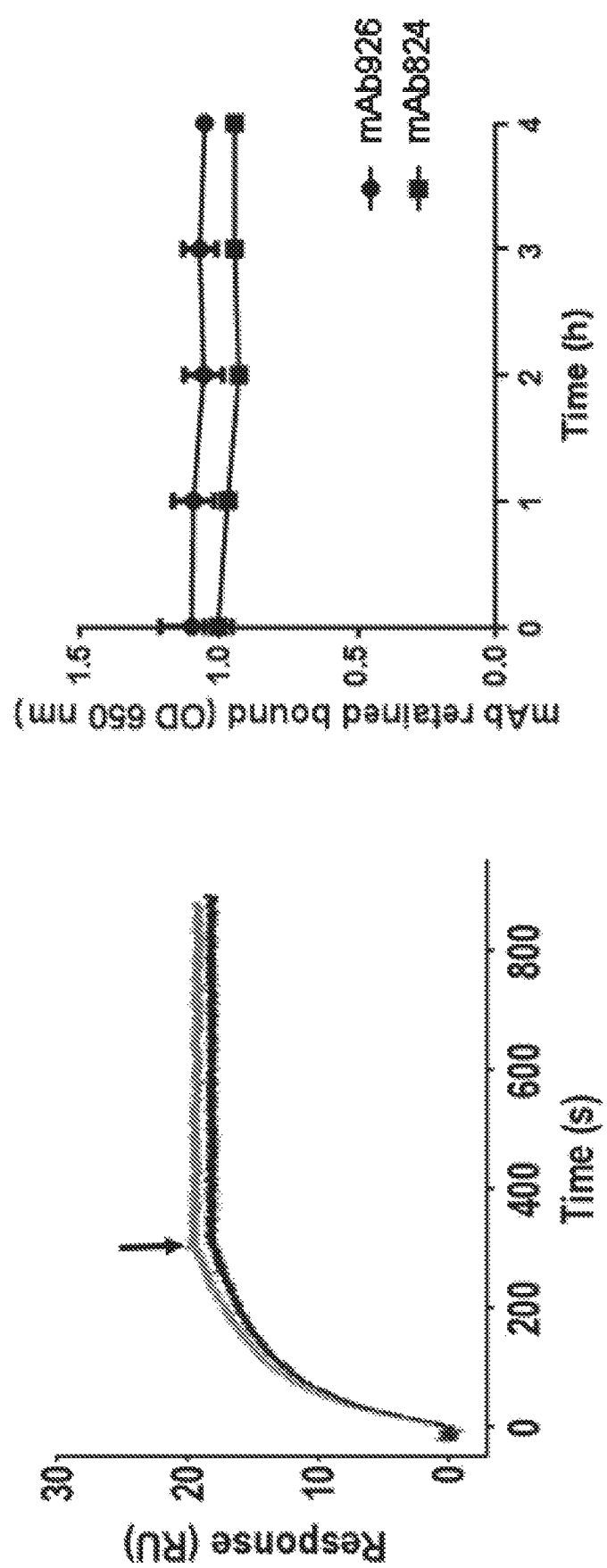

FIG. 18. Binding to and dissociation of mAbs from fimbrial FimH. (A) Binding of mAb824 to CM5 chip-immobilized fimbriae with FimH$^{wt}$ recorded by SPR. The mAb824 at concentration 200 nM was allowed to bind in two parallel channels for 300 s. At the time designated by the arrow, either running buffer (black curve) or running buffer with 1% mannose (grey curve) was injected for the next 600 s. Single replicate for each condition (+/−mannose) is shown. (B) Dissociation of FimH$^{wt}$-bound antibodies upon 1-4 h-long incubation in PBS as determined by ELISA. Data are mean±SD (n=2 independent experiments).

DETAILED DESCRIPTION OF THE INVENTION

The invention is based on the surprising and unexpected discovery of a type of inhibitory monoclonal antibody against the mannose-binding adhesin of $E.\ coli$, FimH, that does not fall into either of the known two categories of inhibitors. Like an allosteric inhibitor, this antibody exerts non-competitive inhibition, but like an orthosteric inhibitor, it binds within the ligand-binding pocket. Unlike the latter, however, it forces the conversion of the binding pocket to an open, inactive conformation, even when the pocket is occupied by the ligand mannose.

As described herein, we compared the inhibitory mechanism of different anti-FimH antibodies and describe an antibody that blocks the adhesive function in a distinct manner consistent with the parasteric model of inhibition. Compared to an orthosteric antibody, the parasteric antibody was a more potent inhibitor against bacterial adhesion, surface-bound biofilms and in vivo colonizations, demonstrating that design of parasteric inhibitors potentially represents a very powerful approach toward the development of anti-adhesive preventive and therapeutic strategies.

The antibodies of the invention inhibit bacterial adhesion with an IC50 as low as 0.4 nM. Described herein are methods and antibody compositions for displacing mannose from the binding pocket of fimbrial adhesin FimH of enterobacteria, such as uropathogenic *E. coli, Klebsiella oxytoca*, or *Klebsiella pneumoniae*. The antibodies of the invention bind within the mannose-binding pocket of FimH and are able to compete with mannose for binding to FimH, or to release mannose bound to the pocket in a non-competitive manner, for example, by binding to a side of the pocket. The antibody can thus prevent attachment of bacteria to a mannose-coated surface, and also detach bacteria already attached to a mannose-coated surface. The antibody can be used to disrupt or prevent the attachment of a single layer of bacteria to a mannose-coated surface, or to disrupt or prevent the formation of a multilayer biofilm. The antibody compositions of the invention can thus be used in methods to inhibit, prevent, or reverse the colonization of a surface with enterobacteria that express the bacterial Type 1 fimbrial adhesin FimH, to inhibit or prevent infection of a cell by enterobacteria that express the bacterial Type 1 fimbrial adhesin FimH, such as, for example, uropathogenic *E. coli*, to treat a bacterial infection in subject in need thereof, and to treat or prevent inflammatory bowel disease (IBD).

Definitions

As used herein, "antibody" refers to monoclonal antibodies, polyclonal antibodies, multispecific antibodies (e.g., bispecific antibodies), and antibody fragments so long as they exhibit the desired antigen-binding activity. An "antibody fragment" refers to a molecule other than an intact antibody that comprises a portion of an intact antibody and that binds the antigen to which the intact antibody binds. Examples of antibody fragments include, but are not limited to, Fv, Fab, Fab', Fab'-SH, F(ab')2; diabodies; linear antibodies; single-chain antibody molecules (e.g. scFv); and multispecific antibodies formed from antibody fragments.

As used herein, "specifically binds" refers to the binding of an antibody to a specific protein or target which is present amongst a heterogeneous population of proteins. Hence, when present in specific immunoassay conditions, the antibodies bind to a particular protein target, such as FimH, and do not bind in a significant amount to other proteins present in the sample.

As used herein, "identical" means, with respect to amino acid sequences, that at any particular amino acid residue position in an aligned sequence, the amino acid residue is identical between the aligned sequences. The term "similarity" or "sequence similarity" as used herein, indicates that, at any particular position in the aligned sequences, the amino acid residue is of a similar type between the sequences. For example, leucine may be substituted for an isoleucine or valine residue. This type of substitution can be referred to as a conservative substitution. Preferably, a conservative substitution of any of the amino acid residues contained in a given amino acid sequence, these changes have no effect on the binding specificity or functional activity of the resulting antibody when compared to the unmodified antibody.

As used herein, "corresponding position" refers to an amino acid residue that is present in a second sequence at a position corresponding to a specified amino acid residue in a first sequence which is the same position as the position in the first sequence when the two sequences are aligned to allow for maximum sequence identity between the two sequences.

As used herein, "consists essentially of" or "consisting essentially of" means that a polypeptide may have additional features or elements beyond those described, provided that such additional features or elements do not materially affect the ability of the antibody or antibody fragment to have the recited binding specificity. The antibody or antibody fragments comprising the polypeptides may have additional features or elements that do not interfere with the ability of the antibody or antibody fragments to bind to its target and exhibit its functional activity, e.g., disrupting or preventing bacterial adhesion to a mannose-coated surface. Such modifications may be introduced into the amino acid sequence in order to reduce the immunogenicity of the antibody. For example, a polypeptide consisting essentially of a specified sequence may contain one, two, three, four, five or more additional, deleted or substituted amino acids, at either end or at both ends of the sequence provided that these amino acids do not interfere with, inhibit, block or interrupt the role of the antibody or fragment in binding to its target and exhibiting its biological activity.

As used herein, a "heterologous" sequence or a "heterologous" molecule refers to a moiety not naturally occurring in conjunction with a recited sequence or molecule. Representative examples of the heterologous molecule include, but are not limited to, a polypeptide, antibody, epitope, polynucleotide, small molecule or drug. Such heterologous moieties can be useful for improving solubility, delivery, immunogenicity, efficacy, detection, or identification of the recited sequence or molecule. In some embodiments, the heterologous sequence is inert or an unrelated sequence. A moiety which contributes to antibodies of the invention may be chemically modified with one or more functional groups, provided that such functional groups do not interfere with the ability of the antibody or antibody fragment to bind to FimH and disrupt or prevent bacterial adhesion to a mannose-coated surface.

As used herein, "enterobacteria" (or enterobacteriaceae) refers to gram-negative bacteria that express the bacterial Type 1 fimbrial adhesin FimH. Examples of enterobacteria include, but are not limited to, *E. coli, K. pneumoniae, K. oxytoca, Shigella, Serratia spp, Enterobacter spp, Citrobacter*, and *Edwardsiella*.

As used herein, "inflammatory bowel disease" (or IBD) refers to inflammatory conditions of the colon and small intestine, including, but not limited to, Crohn's disease and ulcerative colitis.

As used herein, "pharmaceutically acceptable carrier" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline.

Compositions comprising such carriers are formulated by well-known conventional methods (see, for example, Remington's Pharmaceutical Sciences, 18th edition, (Remington and Gennaro 1990)).

As used herein, to "prevent" or "treat" a condition means to decrease or inhibit symptoms indicative of the condition or to delay the onset or reduce the severity of the condition.

As used herein, "adjuvant" includes those adjuvants commonly used in the art to facilitate an immune response. In some embodiments, such as with the use of a polynucleotide vaccine, an adjuvant such as a helper peptide or cytokine can be provided via a polynucleotide encoding the adjuvant.

As used herein, "a" or "an" means at least one, unless clearly indicated otherwise.

As used herein, the terms "comprise" or "include", or variations such as "comprises" or "comprising", "includes" or "including" mean the inclusion of a recited item or group of items, but not the exclusion of any other item or group of items.

Methods and Uses of the Invention

In one embodiment, the invention provides a method to inhibit, prevent, or reverse the colonization of a surface with enterobacteria that express the bacterial Type 1 fimbrial adhesin FimH. Examples of enterobacteria include, but are not limited to, *E. coli, K. pneumoniae, K. oxytoca, Shigella, Serratia spp, Enterobacter spp, Citrobacter*, and *Edwardsiella*. The surface can be a biological or non-biological surface. Examples of biological surfaces that can be colonized by enterobacteria include, but are not limited to, mucosal epithelial surfaces. Examples of non-biological surfaces that can be colonized by enterobacteria include, but are not limited to, catheters and intubation devices. The method typically comprises contacting the surface with a composition comprising an antibody of the invention.

In one embodiment, the invention provides a method to inhibit or prevent infection of a cell by enterobacteria that express the bacterial Type 1 fimbrial adhesin FimH, such as, for example, uropathogenic *E. coli*. The method comprises administering to a tissue infected with the enterobacteria, e.g., uropathogenic *E. coli*, or other species of *E. coli, K. pneumoniae, K. oxytoca, Shigella, Serratia spp, Enterobacter spp, Citrobacter*, and *Edwardsiella*. The method comprises contacting the cell with an effective amount of a composition of the invention, thereby inhibiting or preventing infection of the cell.

In one embodiment, the invention provides a method to treat a bacterial infection in subject in need thereof, wherein the subject is infected with enterobacteria such as *E. coli, K. pneumoniae, K. oxytoca, Shigella, Serratia spp, Enterobacter spp, Citrobacter*, and *Edwardsiella*. In some embodiments, the enterobacteria is uropathogenic *E. coli, Klebsiella oxytoca*, or *Klebsiella pneumoniae*. The method comprises administering to the subject an effective amount of a composition as described herein, thereby treating a bacterial infection in the subject. In some embodiments, the bacterial infection is colitis or sepsis. Additional representative examples of infections to be treated by the method include, but are not limited to, pneumonia, including ventilated pneumonia in intubated patients, catheter-associated infections, including urinary and blood line catheters, newborn meningitis, urinary tract infections, including those resulting from vaginal and periurethral colonization, and wound infections.

In one embodiment, the invention provides a method of treating or preventing inflammatory bowel disease (IBD) in a subject. The method comprises administering to the subject an effective amount of a composition as described herein, thereby treating or preventing IBD in the subject. In one embodiment, the administering is by subcutaneous, topical, transdermal, intravenous, oral, or intracolonic administration.

Antibodies and Compositions of the Invention

In one embodiment, the invention provides a composition comprising an antibody or polynucleotide encoding same that specifically recognizes and binds uropathogenic *Escherichia coli* (*E. coli*) fimbrial adhesin FimH and is capable of preventing colonization of a surface by uropathogenic *E. coli*. In one embodiment, the antibody comprises a light chain variable region, and, optionally, a heavy chain variable region. In a typical embodiment, the light chain variable region comprises an amino acid sequence selected from the group consisting of SEQ ID NO: 1, SEQ ID NO: 3, and sequences at least 90% identical thereto. The light chain variable region comprises one, two or three of three complementarity determining regions (CDRs), CDR1, CDR2, and CDR3. The CDR1 sequence comprises QNVSN (residues 27-31 of SEQ ID NO: 1) or QNIVHNNGNTY (residues 27-37 of SEQ ID NO: 3). The CDR2 sequence comprises SAS (residues 49-51 of SEQ ID NO: 1) or KVS (residues 55-57 of SEQ ID NO: 3). The CDR3 sequence comprises QQNSSFPFT (residues 88-96 of SEQ ID NO: 1) or FQGSHVPFT (residues 94-102 of SEQ ID NO: 3). In a typical embodiment, the heavy chain variable region comprises an amino acid sequence selected from the group consisting of SEQ ID NO: 2, SEQ ID NO: 4, and sequences at least 90% identical thereto. The heavy chain variable region comprises one, two or three of three complementarity determining regions (CDRs), CDR1, CDR2, and CDR3. The CDR1 sequence comprises GYAFSSYW (residues 26-33 of SEQ ID NO: 2) or GYTSTNYW (residues 26-33 of SEQ ID NO: 4). The CDR2 sequence comprises IYPRDGDT (residues 51-58 of SEQ ID NO: 2) or INPTSGYT (residues 51-58 of SEQ ID NO: 4). The CDR3 sequence comprises EVGRGFYGMDY (residues 97-107 of SEQ ID NO: 2) or ARGVIRDF (residues 97-104 of SEQ ID NO: 4).

In some embodiments, the amino acid sequence of the light chain variable region has at least 95% identity with SEQ ID NO: 1 or 3. Representative examples of the amino acid sequence of the light chain variable region include, but are not limited to, the group consisting of: SEQ ID NO: 1, 3, 5, and 6. In some embodiments, the amino acid sequence of the light chain variable region is SEQ ID NO: 3.

In some embodiments, the amino acid sequence of the heavy chain variable region sequence has at least 95% identity with SEQ ID NO: 2 or 4. Representative examples of the amino acid sequence of the heavy chain variable region include, but are not limited to, the group consisting of: SEQ ID NO: 2, 4, 6, and 8. In some embodiments, the amino acid sequence of the heavy chain variable region is SEQ ID NO: 4.

In one embodiment, the antibody binds within the mannose-binding pocket of the uropathogenic *E. coli* FimH. In a typical embodiment, the antibody binds within amino acid residues 133-142 of the FimH amino acid sequence shown in SEQ ID NO: 14. In some embodiments, the antibody binds a conformational epitope selected from 152, N135, N136, Y137, N138, and D140 of SEQ ID NO: 14; and F1, N46, I52, D54, Q133, N135 and N136 of SEQ ID NO: 14. SEQ ID NO: 14 is the amino acid sequence of FimH of K12. SEQ ID NO: 15 is the amino acid sequence of FimH of UTI89, which differs by only a few residues, as shown below.

Amino Acid Sequence of FimH of K12 (upper rows) and UTI89 (lower rows):

```
            10         20         30         40
    ....|....|....|....|....|....|....|....|
    FACKTANGTAIPIGGGSANVYVNLAPVVNVGQNLVVDLST
    ............................A..........

50         60         70         80
    ....|....|....|....|....|....|....|....|
    QIFCHNDYPETITDYVTLQRGSAYGGVLSNFSGTVKYSGS
    ....................A........S.......N..

90        100        110        120
    ....|....|....|....|....|....|....|....|
    SYPFPTTSETPRVVYNSRTDKPWPVALYLTPVSSAGGVAI
    ........................................

130        140        150        160
    ....|....|....|....|....|....|....|....|
    KAGSLIAVLILRQTNNYNSDDFQFVWNIYANNDVVVPTGG
    ........................................

170        180        190        200
    ....|....|....|....|....|....|....|....|
    CDVSARDVTVTLPDYPGSVPIPLTVYCAKSQNLGYYLSGT
    ........................................

210        220        230        240
    ....|....|....|....|....|....|....|....|
    TADAGNSIFTNTASFSPAQGVGVQLTRNGTIIPANNTVSL
    ........................................

250        260        270
    ....|....|....|....|....|....|....|
    GAVGTSAVSLGLTANYARTGGQVTAGNVQSIIGVT
    ..................................

280
    ....|
    FVYQ*  SEQ ID NO: 14
    ....*  SEQ TD NO: 15
```

In one particular embodiment, the antibody binds within the mannose-binding pocket of FimH and thereby competes with mannose for binding to FimH. In another particular embodiment, the antibody binds within the mannose-binding pocket of FimH and thereby releases mannose bound to the pocket in a non-competitive manner, for example, by binding to a side of the pocket. In these manners, the antibody can both prevent attachment of bacteria to a mannose-coated surface, and detach bacteria already attached to a mannose-coated surface. The antibody can be used to disrupt or prevent the attachment of a single layer of bacteria to a mannose-coated surface, or to disrupt or prevent the formation of a multilayer biofilm. The invention provides a method of displacing mannose from the binding pocket of fimbrial adhesin FimH of enterobacteria, such as uropathogenic *E. coli, Klebsiella oxytoca,* or *Klebsiella pneumoniae*. In a typical embodiment, the method comprises contacting the binding pocket with a composition of the invention.

In one embodiment, the antibody inhibits bacterial adhesion with an IC50 less than about 15 nM. In another embodiment, the antibody inhibits bacterial adhesion with an IC50 less than 1 nM. In one particular embodiment, the antibody inhibits bacterial adhesion with an IC50 of about 14 nM. In another particular embodiment, the antibody inhibits bacterial adhesion with an IC50 of about 0.4 nM.

In some embodiments, the antibody further comprises a heterologous sequence. Examples of a heterologous sequence include, but are not limited to, sequence encoding all or a portion of a polypeptide, antibody, epitope, or other moiety that would not be found adjacent to the recited sequence under natural conditions. Such heterologous moieties can be useful for improving solubility, delivery, immunogenicity, efficacy, detection, or identification of the recited sequence or molecule. In some embodiments, the heterologous sequence is inert or an unrelated sequence. The antibody can be, for example, one or more of a polyclonal antibody, a monoclonal antibody, a humanized antibody, a human antibody, an antibody derivative, a veneered antibody, a diabody, an antibody derivative, a recombinant human antibody, a chimeric antibody, or an antibody fragment. In one embodiment, the antibody is a monoclonal antibody.

The invention additionally provides polynucleotides encoding antibodies of the invention. Thus, in some embodiments, the antibody composition of the invention comprises a nucleic acid molecule encoding the recited antibody. In some embodiments, one nucleic acid molecule encodes the entire antibody or functional fragment thereof, while in others, separate nucleic acid molecules are provided that encode portions, regions, and/or fragments of the antibody.

In one embodiment, the composition is a pharmaceutical composition. The composition can comprise a therapeutically or prophylactically effective amount of an antibody, or polynucleotide encoding same, of the invention. An effective amount is an amount sufficient to disrupt bacterial adhesion and/or biofilm formation, or to alleviate symptoms of a condition, disease, or infection. In some embodiments, the composition of the invention further comprises a carrier. The carrier can be a pharmaceutically acceptable carrier, or other carrier that facilitates use of the antibody composition.

While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate. Compounds may also be encapsulated within liposomes via known methods.

Administration of the Compositions

Treatment includes prophylaxis and therapy. Prophylaxis or treatment can be accomplished by a single direct injection at a single time point or multiple time points. Administration can also be nearly simultaneous to multiple sites. Patients or subjects include mammals, such as human, bovine, equine, canine, feline, porcine, and ovine animals as well as other veterinary subjects. Typical patients or subjects are human.

Compositions are typically administered in vivo via parenteral (e.g. intravenous, subcutaneous, and intramuscular) or other traditional direct routes, such as buccal/sublingual, rectal, oral, nasal, topical, (such as transdermal and ophthalmic), vaginal, pulmonary, intraarterial, intraperitoneal, intraocular, or intranasal routes or directly into a specific tissue.

The compositions are administered in any suitable manner, often with pharmaceutically acceptable carriers. Suitable methods of administering cells in the context of the present invention to a patient are available, and, although more than one route can be used to administer a particular composition, a particular route can often provide a more immediate and more effective reaction than another route.

The dose administered to a patient, in the context of the present invention should be sufficient to effect a beneficial therapeutic response in the patient over time, or to inhibit infection or disease due to infection. Thus, the composition is administered to a patient in an amount sufficient to alleviate, reduce, cure or at least partially arrest symptoms and/or complications from the disease or infection. An amount adequate to accomplish this is defined as a "therapeutically effective dose."

The dose will be determined by the activity of the composition produced and the condition of the patient, as well as the body weight or surface areas of the patient to be treated. The size of the dose also will be determined by the existence, nature, and extent of any adverse side effects that accompany the administration of a particular composition in a particular patient. In determining the effective amount of the composition to be administered in the treatment or prophylaxis of diseases such as enterobacterial infection, the physician needs to evaluate the progression of the disease, and any treatment-related toxicity.

Kits

For use in the methods described herein, kits are also within the scope of the invention. Such kits can comprise a package or container that is compartmentalized to receive one or more containers such as vials, tubes, and the like, each of the container(s) comprising one of the separate elements (e.g., antibodies, carriers) to be used in the method. Typically, the kit comprises one or more antibodies or polynucleotides of the invention. The kit further comprises one or more containers, with one or more antibodies stored in the containers. The kit of the invention will typically comprise the container described above and one or more other containers comprising materials desirable from a commercial and user standpoint, including buffers, diluents, filters, needles, syringes, and package inserts with instructions for use. In addition, a label can be provided on the container to indicate that the composition is used for a specific therapeutic or non-therapeutic application, and can also indicate directions for use. Directions and or other information can also be included on an insert which is included with the kit.

EXAMPLES

The following examples are presented to illustrate the present invention and to assist one of ordinary skill in making and using the same. The examples are not intended in any way to otherwise limit the scope of the invention.

Example 1: Anti-FimH Antibodies mAb926 and mAb475 Inhibit Bacterial Adhesion with Different Efficiencies and Mechanisms This example describes in greater detail the activity of anti-FimH inhibitory antibodies raised against the lectin domain of FimH in the inactive conformation characterized in a previous study that described the mAb475 antibody that directly competes with mannose binding (Kisiela, et al. 2013). Using IMGT/V-Quest software (Brochet, et al. 2008; Giudicelli, et al. 2011) we now have compared the germline origins of mAb475 and several other FimH-inhibiting monoclonal antibodies. One of the antibodies, mAb926, was of a different germline origin from mAb475, with the amino acid sequence homology of the VL- and VH regions being only 56% and 71%, respectively, and all three complementarity-determining regions being highly diverse (FIG. 13). We therefore compared the abilities of mAb926 and mAb475 to inhibit FimH in greater detail.

Figure 1:
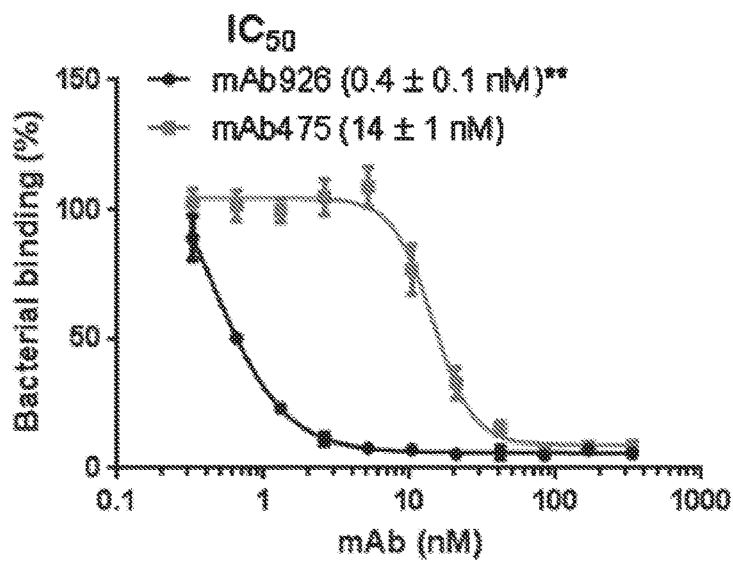
FIG. 1. Inhibitory potency of mAb926 and mAb475. Binding of FimH$^{wt}$-expressing *E. coli* to surface-immobilized yeast mannan in the presence of different concentrations of anti-FimH antibodies. Data are mean±SEM (n=5 independent experiments). The IC50 values were calculated from the fitted curves shown using Prism GraphPad 6 software. **, P≤0.005 (t-test).

Type 1 fimbriated bacterial cells expressing the wild-type FimH adhesin variant of the uropathogenic E. coli strain J96 (FimH$^{wt}$) were pre-incubated with different concentrations of the antibodies and then allowed to bind to mannosylated surfaces (FIG. 1). mAb926 inhibited bacterial adhesion with half-maximal inhibitory concentration (IC50) of 0.4±0.1 nM and mAb475 with IC50 of 14±1 nM indicating much higher inhibitory potency of mAb926 (FIG. 1). To determine if the 32-fold difference (P≤0.005) in inhibitory potency of the antibodies reflected a difference in binding affinity, we characterized binding of the antibodies to the purified fimbriae carrying FimHwt with surface plasmon resonance. As shown in FIG. 14, the $K_D$ of mAb926 was 7-fold lower than $K_D$ of mAb475 (0.58 vs. 4.15 nM, respectively). Thus, the difference in IC50 between the two antibodies could not be explained by a difference in affinity. Indeed, mAb926 demonstrates >50% inhibition at its $K_D$ concentration, while mAb475 demonstrates no measurable inhibition at its $K_D$ concentration (FIG. 1). Moreover, because mAb926 had a 17.6-fold higher association rate relative to mAb475 (49.7 vs. 2.8×104 M-1 s-1, respectively), and a 2.5-fold higher dissociation rate (2.89 vs. 1.17×10-4 s-1, respectively), the difference in affinity was due to the faster association rate of mAb926. The SPR experiments were performed in parallel at the Analytical Biopharmacy Core, at the University of Washington (with separate preparations of the antigenic substrate), with results that are completely consistent with those reported here, adding confidence to our analyses (Table 1). Since in the inhibition assay the antibodies were pre-incubated with the bacteria for one hour, the saturation of binding has likely been reached for both antibodies. Thus, at that point the difference in the dissociation rate of the inhibitory antibodies would be more important than their association rates, so the increased effectiveness of mAb926 is even more remarkable considering its slightly higher dissociation rate.

Thus, taken together, these results demonstrate that the significantly higher inhibitory potential of mAb926 than of mAb475 antibodies cannot be explained by differences in binding kinetics or affinity of the two antibodies. Instead, the large difference in inhibitory potency must reflect some unknown difference in the mechanism of inhibition.

TABLE 1

The binding parameters of mAb926 and mAb475 as measured by surface plasmon resonance.

| | SPR1 (data from FIG. 14) | | | SPR2* | | |
|---|---|---|---|---|---|---|
| | $K_D$ (nM) | $k_a$ ×10⁴ (M⁻¹s⁻¹) | $k_d$ ×10⁻⁴ (s⁻¹) | $K_D$ (nM) | $k_a$ ×10⁴ (M⁻¹s⁻¹) | $k_d$ ×10⁻⁴ (s⁻¹) |
| mAb926 | 0.58 | 49.7 | 2.89 | 0.22 | 99.6 | 217 |
| mAb475 | 4.15 | 2.82 | 1.17 | 1.5 | 8.68 | 1.3 |
| mab926 vs mab475 (fold difference) | 7.2 - lower | 17.6 - higher | 2.5 - higher | 6.8 - lower | 11.5 - higher | 1.7 - higher |

*SPR2 measurements performed at the Analytical Biopharmacy Core, UW Seattle. Experiments were run in HBS-EP buffer using Biacore T100 system (GE/Healthcare). FimH$^{wt}$ fimbriae in 10 mM glycine, pH = 2.6 were immobilized on a Series S CM5 Chip (GE Healthcare) at 1231 RUs using a contact time of 14 minutes. Following immobilization, a flow rate of 30 μL/min, mAb analyte concentrations, ranging from 0 μM to 938 μM were tested in triplicates using a contact time of 60 seconds and a dissociation time of 900 seconds. Each run was followed with three 30-second injections of glycine pH = 1.5 to regenerate the surface. Both the reference surface signal and the blank injection signal were subtracted from the resulting data, and the kinetic data "double referenced" in this manner was fitted globally across all concentrations to a 1:1 Langmuir binding model using the Biacore T200 Evaluation Software (GE Healthcare version 2.0).

Example 2: Mannose Directly Competes with mAb475 but not mAb926 Binding

This Example compares the ability of mAb475 and mAb926 to bind FimH in the presence of soluble mannose. As shown in FIG. 2A, mannose strongly inhibited mAb475 binding, causing a significant shift of its binding curve towards higher concentrations of the antibody. The mAb475 half-maximal effective concentration ($EC_{50}$) increased 179-fold in the presence of soluble mannose. In contrast, binding of mAb926 was affected by mannose to a much lesser extent resulting in a relatively small rightward shift of the binding curve with a 6.2-fold increase in the mAb926 $EC_{50}$ (FIG. 2B).

To distinguish between competitive versus non-competitive interactions of mannose and the antibodies, we compared the observed $EC_{50}$ ratio values for antibody binding with an $EC_{50}$ ratio for a model of two ligands binding to a receptor (Ehlert 1988). Based on the model, mannose and antibody can compete for binding to the same site on FimH according to their relative concentrations and affinities, or bind to the receptor simultaneously (FIG. 15) with the affinities altered by a cooperativity factor α (Kenakin 2004). The calculated $EC_{50}$ ratio for competitive binding (see Material and Methods) was 175±30, which is consistent with the $EC_{50}$ ratio experimentally determined for mAb475 (179) confirming that the antibody is a direct competitor. Thus, binding of mAb475 and mannose to FimH is not simultaneous but mutually exclusive, implying binding to a structurally identical site, consistent with our previously reported determination of the mAb475 epitope (Kisiela, et al. 2013). However, the 6.2-fold alteration of mAb926 $EC_{50}$ by mannose cannot be explained by the competitive inhibition model but instead indicates that mannose inhibits mAb926 binding in a non-competitive manner consistent with simultaneous binding of the antibodies and mannose to FimH.

The non-competitive relationship of mAb926 with the mannose ligand indicates that, unlike with mAb475, inhibition of FimH activity by mAb926 is not via a direct orthosteric mechanism. It rather resembles more the mechanism exerted by allosteric inhibitors that, however, would have to involve structurally distant sites for antibody and ligand binding.

Inhibitory mAb475 and mAb926 recognize overlapping but distinct epitopes within the mannose-binding pocket of the active FimH conformation.

Figure 3:
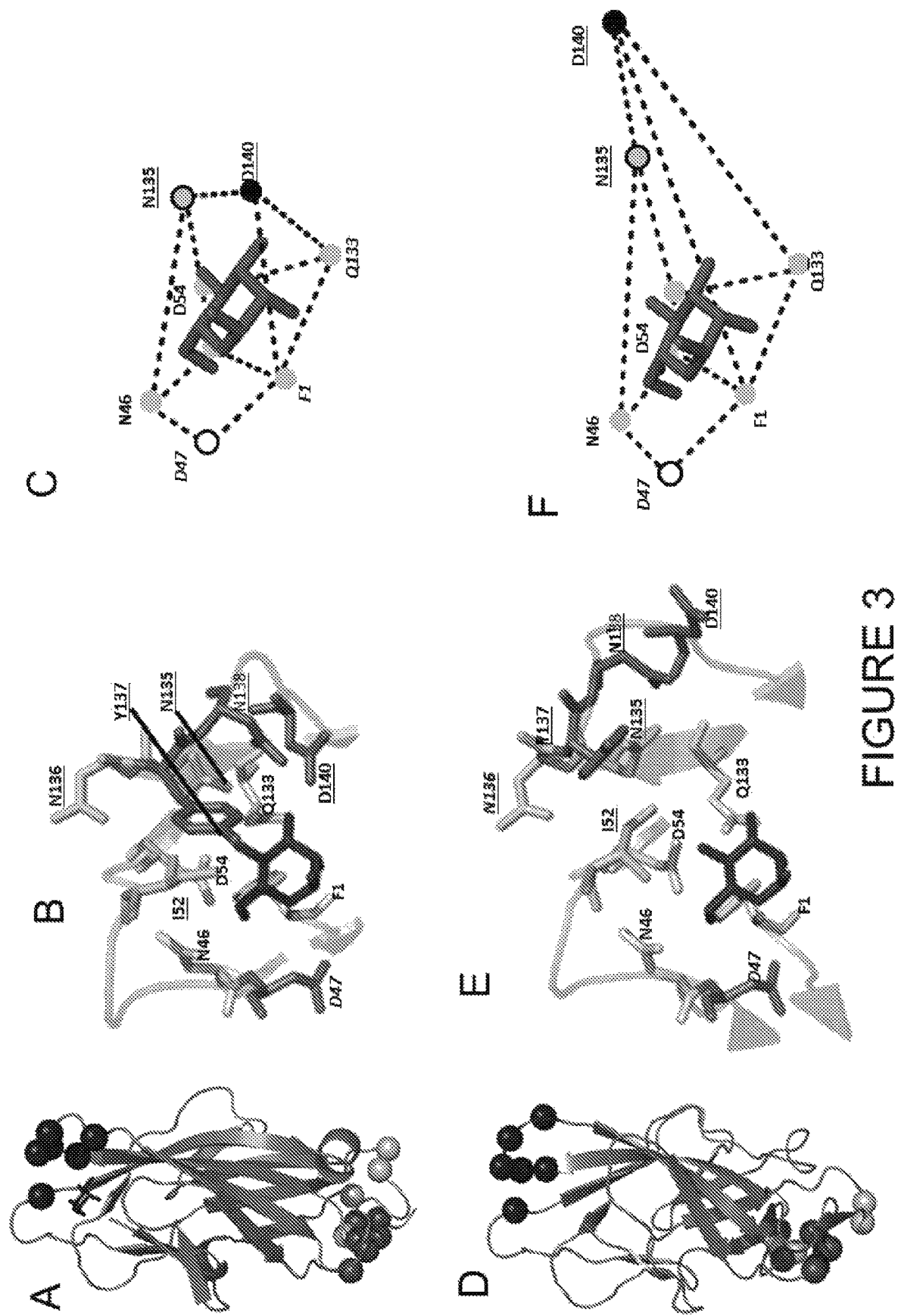
FIG. 3. Inhibitory antibodies mAb926 and mAb475 recognize epitopes differently overlapping the mannose-binding pocket of FimH. Epitope of mAb926 mapped on crystal structure of the active (A) and inactive (D) conformations of the FimH lectin domain. Ca atoms of mAb926 epitope residues are shown as black spheres. The natural allosteric site (residues V28, V30, S114 and A115) (Le Trong, et al. 2010) is shown as light grey spheres and D-mannose is shown as black sticks. The epitope of mAb21 is shown as dark grey spheres. (B and E) Close-up of FimH binding pocket with mAb926 and mAb475 epitopes presented as sticks. The mAb926 epitope residues are underlined and mAb475 epitope residues are in bold. The overlapping residues of these two epitopes are underlined and in bold. D47 residue, involved in direct hydrogen bond with D-mannose but not being a part of either mAb epitope is italicized. (C and F) Relative distances between mannose-contacting amino acid residues in the active and the inactive FimH conformations, respectively. The crystalized and the computationally docked (see text) positions of D-mannose (dark grey sticks) are also shown. The presented distances were measured between heavy atoms of residue side chains that are known to form hydrogen bonds with D-mannose ligand (Hung, et al. 2002). The PDB codes for active- and the inactive structures are 1UWF and 3JWN, respectively. The position of D-mannose in the 1 UWF was determined by alignment with the sugar ring of butyl α-D-mannoside of the original crystal structure.

We next determined the mAb926 binding epitope in FimH by site-directed mutagenesis (Table 2) and compared it with the locations of the mAb475 epitope and mannose-interacting residues of the adhesin defined according to lectin domain crystalized in the high-affinity (active), mannose-bound conformation (FIG. 3A).

TABLE 2

Mapping of mAb926 epitope using FimH mutant library.

| Mutation | mAb binding relative to wild type* (%) |
|---|---|
| F1L | 111 |
| A2S | 92 |
| P12A | 87 |
| I13S | 66 |
| H45A | 91 |
| N46A | 90 |
| N46Q | 104 |
| D47S | 97 |
| Y48A | 58 |
| E50A | 69 |
| T51A | 96 |
| I52A | 19 |
| T53A | 100 |
| D54E | 119 |
| Y55A | 99 |
| T57G | 96 |
| I130A | 82 |
| R132D | 102 |
| Q133N | 100 |
| T134G | 122 |
| N135I | 6 |
| N136A | 13 |
| Y137A | 2 |
| N138I | 8 |
| S139A | 105 |
| D140A | 21 |
| D141A | 73 |
| F142A | 100 |

*Binding of mAb926 to purified isogenic fimbriae with different mutations in LD of FimH (FimH$^{wt}$(186-201)$^{FocH}$) was tested as described in Materials and Methods. Predicted mAb926 epitope residues mutation of which reduced the mAb binding >25% (and which also clustered together on FimH crystal structure) are marked in bold type.

Alteration of positions 52. 135-138 and 140 in FimH abrogated mAb926 binding (Table 2 and Table 3). These positions form a compact epitope located on the top of the lectin domain (FIG. 3A, black spheres), i.e. on the side of the beta-barrel where the mannose-binding pocket is positioned. This epitope location is opposite from the domain-domain interaction interface that comprises the natural allosteric site of the lectin domain (FIG. 3A, light grey spheres) (Le Trong, et al. 2010). Three out of 6 of the residues in the mAb926 epitope, I52, N135 and N136, are also part of the mAb475 epitope (which include positions 1 46, 52, 54, 133, 135, and 136) (Table 3 and FIG. 3B) (Kisiela, et al. 2013). The predicted structural overlap of mAb926 and mAb475 epitopes is also supported experimentally by the fact that mAb926 and mAb475 strongly cross-interfere with each other's binding to FimH (FIG. 16).

TABLE 2

The overlap between the FimH pocket residues and mAb926 and mAb475 epitopes. Distances between mannose ligand and hydrogen bond forming FimH amino acids in the active and inactive conformation of the binding pocket are also shown.

| FimH AA | Epitope | | α-man-FimH AA hydrogen bond distance (Å)[1] | | |
|---|---|---|---|---|---|
| | mAb926 | mAb475 | α-man atom | FimH conformation | |
| | | | | Active | Inactive |
| Phe1 | | + | O2/O5/O6 | 2.9/2.9/2.8 | 2.9/3/2.8 |
| Asn46 | | + | O6 | 3.1 | 3 |
| Asp47 | | + | O6 | 2.9 | 3.1 |
| Ile52* | + | + | — | — | — |
| Asp54 | | + | O4/O6 | 2.5/2.5 | 2.7/2.6 |
| Gln133 | | + | O3 | 3.1 | 3.1 |
| Asn135 | + | + | O3/O4 | 3.6/2.9 | 6.2/6.2 |
| Asn136 | + | + | — | — | — |
| Tyr137* | + | | — | — | — |
| Asn138 | + | | — | — | — |
| Asp140 | + | | O3 | 2.6 | 9.9 |

[1]Distance between hydrogen bond forming atoms of α-D-mannose and FimH amino acid residues in the active-(1UWF) and the inactive (3JWN) conformers of lectin domain as measured by PyMole.
*AA involved in hydrophobic interactions with mannose.

Epitopes of both antibodies overlap with the mannose-binding pocket (Table 3 and FIG. 3B), in particular with the network of 7 side chain residues that form 11 hydrogen bonds with the ligand (Hung, et al. 2002). However, the mAb475 epitope is positioned on at least three different areas of the pocket (46-54 and 133-142 loops and N-terminal end) and includes a total of 5 of these mannose-interacting residues that form a total of 9 hydrogen bonds with the ligand (Hung, et al. 2002; Kisiela, et al. 2013). In contrast, almost the entire mAb926 epitope is limited to just one side of the pocket formed by loop 133-142, with only two residues—135 and 140—forming a total of 3 hydrogen bonds with mannose. Consistent with structural data, mutation of residues that are directly (N135 and D140)- or indirectly (N138) involved in hydrogen bonds with ligand substantially decreased ligand binding (Hung, et al. 2002; Kisiela, et al. 2013; Nilsson, et al. 2006b), while mutation of remaining mAb926 epitope residues had no or only minor effect on the interactions with mannose (Kisiela, et al. 2013).

Thus, the epitope of non-competitively inhibiting mAb926 overlaps with the mannose-binding pocket of the active FimH but, in contrast to the mAb475 epitope, is mostly limited to just one loop of the pocket. Still, because two residues of the mAb926 epitope contribute to the network of hydrogen bonds with the mannose ligand, it is plausible to expect some inhibitory effect of mAb926 against mannose binding, consistent with results reported above.

Example 3: The mAb926 Epitope Shifts Away from Mannose-Interacting Residues in the Inactive FimH While the overlap of mAb926 epitope with the mannose-binding residues in the active FimH explains the inhibitory potential of the antibody, it does not explain the non-competitive nature of the mAb926 inhibition. Thus, we turned to the alternative FimH structure (3JWN), where the lectin domain assumed a more twisted conformation and interacts with the pilin domain (FIG. 3D). This structure was obtained in the absence of mannose ligand and its binding pocket is in an open, low-affinity (i.e. inactive) conformation.

As the inactive FimH structure was obtained in the absence of ligand, we first determined the potential position for mannose in the open configuration of binding pocket.

Mannose was docked into the pocket of the 3JWN crystal structure using coordinates present in the active 1UWF structure followed by energy minimization using the CHARMM and the PARAM22 force field. As shown in Table 3 and FIG. 3E mannose is predicted to take a position in the open pocket that retains 8 out of 11 hydrogen interactions of the active FimH with side chains of 5 out of 7 mannose-interacting residues—Phe1, Asn46, Asp47, Asp54 and Gln133 (Hung, et al. 2002). Interestingly, these five residues in the inactive binding pocket retain essentially the same position relative to each other as in the active FimH (FIGS. 3C and 3F), with the distance shift being 0.1 to 1 Å (0.44 Å±0.3 on average)(FIG. 17). This position of mannose is also supported by previous studies that employed molecular dynamics simulations of the active pocket or resolved crystal structure of mutationally inactivated FimH (Hung, et al. 2002; Nilsson, et al. 2008).

According to the predicted position of mannose, two of the residues that interact with mannose in the active structure—Asn135 and Asp140—would lose their contacts with mannose in the open binding pocket (FIG. 3E and Table 3). In the alternative FimH structures, these two residues also shifted significantly relative to one another and the other five mannose-interacting residues (FIG. 3F), with the shift being 1.2 to 7.7 Å (3.9±2.2 Å on average) (FIG. 17).

Thus, based on the projected mannose position in the inactive FimH, the mAb926 epitope residues that form hydrogen bonds with mannose in the active conformation are shifted relatively further away from the ligand in the inactive conformation. Thus, while in the active FimH pocket a portion of the mAb926 epitope is occupied by mannose, in the inactive FimH the entire mAb926 epitope is potentially accessible to the antibody.

Example 4: mAb926 Blocks FimH Conversion from Inactive to Active Conformation

Because the mannose binding pocket of FimH is allosterically coupled with the rest of the lectin domain, we compared the effects of mAb926 and mAb475 antibodies on the conformation of FimH. For this, we used the mAb21 antibody that recognizes only the active conformation of FimH. The mAb21 epitope (FIG. 3A, dark grey spheres) is located distal to the mannose-binding pocket and close to the interdomain interface, presumed natural allosteric site (FIG. 3A, light grey spheres) (Le Trong, et al. 2010).

Figure 4:
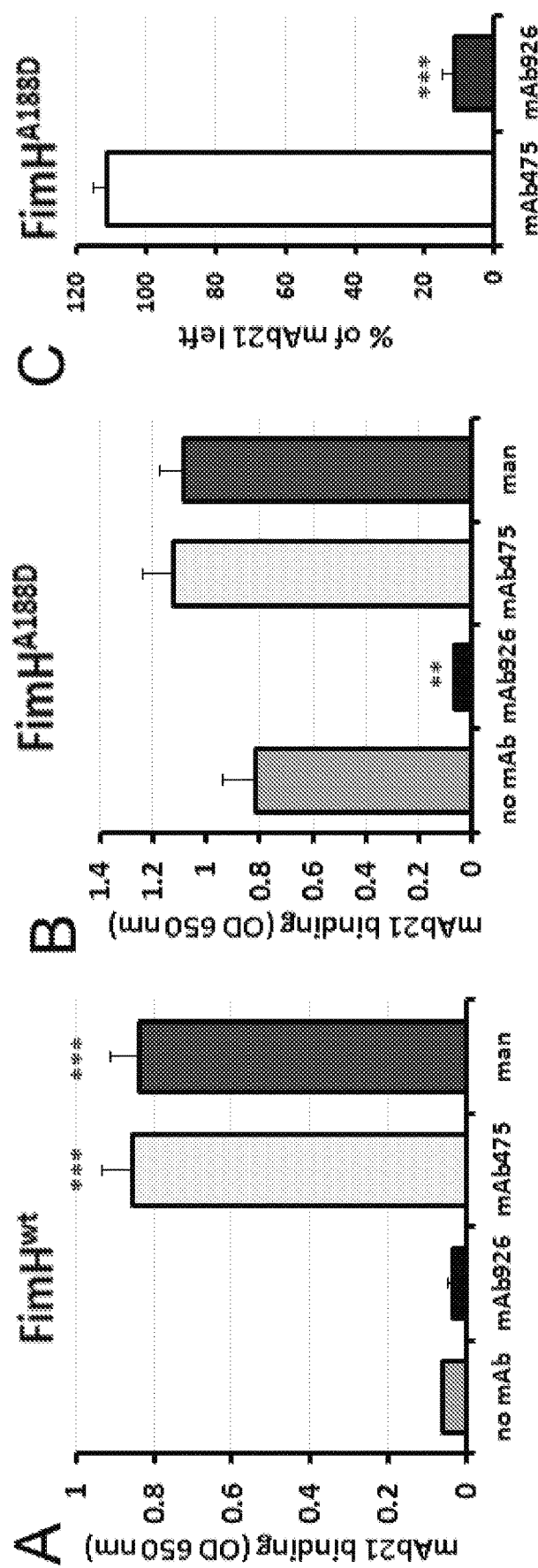
FIG. 4. Effect of antibody binding on FimH conformation. Binding of the active state-specific mAb21 (biotinylated) to fimbrial FimH$^{wt}$ (A) and FimH$^{A188D}$ (B) after pre-treatment with 1% (52 mM) mannose, 50 μg/ml mAb475, or mAb926. (C) Elution of mAb21 (biotinylated) from mAb21-FimHA$^{188D}$ complex 60 minutes after addition of mAb475 or mAb926. Data shown are mean±SEM (n=3 independent experiments). , P≤0.005, *, P≤0.0005 (t-test).

As shown in FIG. 4A, binding of mAb475 and mannose to fimbrial FimH$^{wt}$ converts it from the inactive to the active conformation as determined by binding of active conformation-specific mAb21. In contrast, mAb926 failed to induce such a conversion. We then performed the same experiment but using a FimH mutant variant that has the A188D mutation in the pilin domain that interferes with its interaction with the lectin domain and, in contrast to FimH$^{wt}$, sustains FimH in active state even in the absence of mannose (Tchesnokova, et al. 2008). Pre-treatment of FimH$^{A188D}$ fimbriae with mAb926 entirely abolished its recognition by mAb21 (FIG. 4B), again in sharp contrast with the pretreatment with mAb475 which enhanced subsequent mAb21 binding. Moreover, when FimH$^{A188D}$ was first pre-treated with mAb21 followed by incubation with the inhibitory mAbs, mAb475 stabilized mAb21 binding, while mAb926 resulted in almost complete displacement of the active state-specific antibody from the adhesin (FIG. 4C).

Thus, not only is mAb926 binding to the FimH pocket unable to induce the shift from the inactive to the active conformation of the lectin domain, but it does the opposite—induces a shift away from the active conformation.

Example 5: Mannose can Displace mAb926 but not mAb475 from FimH

Figure 2:
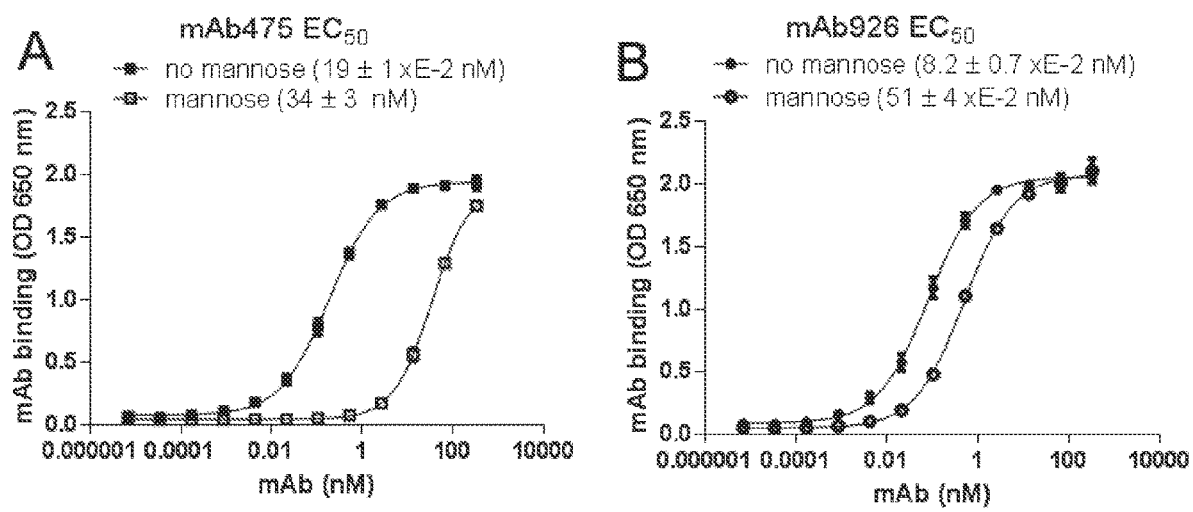
FIG. 2. Effect of mannose on antibody binding. Dose-response curves of mAb475 (A) and mAb926 (B) binding to fimbrial FimHwt in the absence and presence of 1% (52 mM) mannose. The EC50 values were calculated for each mAb separately from the fitted curves shown using Prism Graphpad 6 software. Data shown are mean±SEM (n=3 independent experiments).

In this Example, we assessed whether soluble mannose and mAb926 could interact with the binding pocket simultaneously as predicted by the non-competitive inhibition model. We hypothesized that if mannose and mAb926 do bind together to FimH, then mannose should be able to bind to, and destabilize, a pre-formed complex of FimH with the antibody, resulting in a higher off-rate of mAb926. In contrast, this should not occur for mAb475 bound to FimH as the competitive antibody would fully prevent access of mannose to the pocket and the effect of mannose on the mAb475-FimH complex would be insignificant. In other words, the mannose effect after antibody binding will be opposite from the effect before/during the binding (FIG. 2). Thus, we measured the effect of mannose ligand on the antibody-FimH complexes using surface plasmon resonance.

Figure 5:
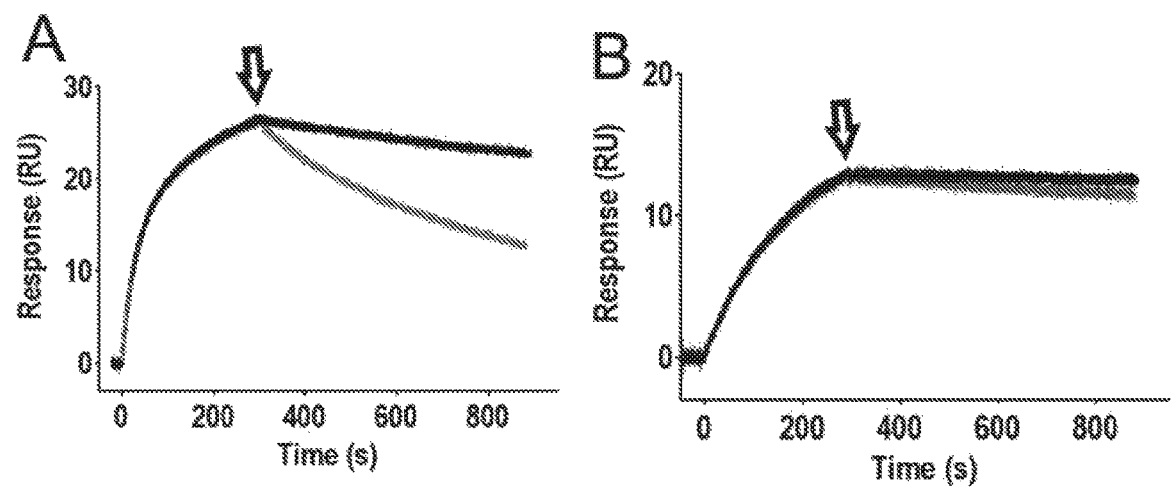
FIG. 5. Effect of mannose on antibodies bound to FimH as determined by surface plasmon resonance. Binding of mAb926 at concentration 50 nM (A) and mAb475 at concentration 100 nM (B) to CM5 chip-immobilized fimbriae with FimH$^{wt}$ was allowed to proceed for 300 s, and running buffer without or with 1% mannose (black and grey curves, respectively) were then injected to the flow cell at the time point designated by arrow, for 600 s. Duplicates for each antibody and conditions tested (+/−mannose) are shown.

Surface coated with FimH$^{wt}$ fimbriae were first allowed to bind mAb926 or mAb475 and then antibody-FimH complexes were exposed to running buffer with and without a high concentration (1%) of soluble mannose. As shown in FIG. 5, the dissociation rate of mAb926 from FimH was dramatically increased in the presence of mannose. At the same time, mannose had no significant effect on the stability of the complexes between mAb475 and FimH over the observed time period.

These results demonstrate that addition of soluble mannose affects the stability of the FimH-mAb926 complex and, thus, the antibody and the ligand must be able to bind to FimH simultaneously, consistent with the non-competitive nature of their interaction. In contrast, there is no such evidence for simultaneous interaction of mannose and mAb475 with FimH consistent with the direct orthosteric inhibitory mechanism of that antibody. Thus, the effect of mannose on the pre-formed antibody-FimH complexes was opposite from the antibodies effect on the complexes formation.

Figure 6:
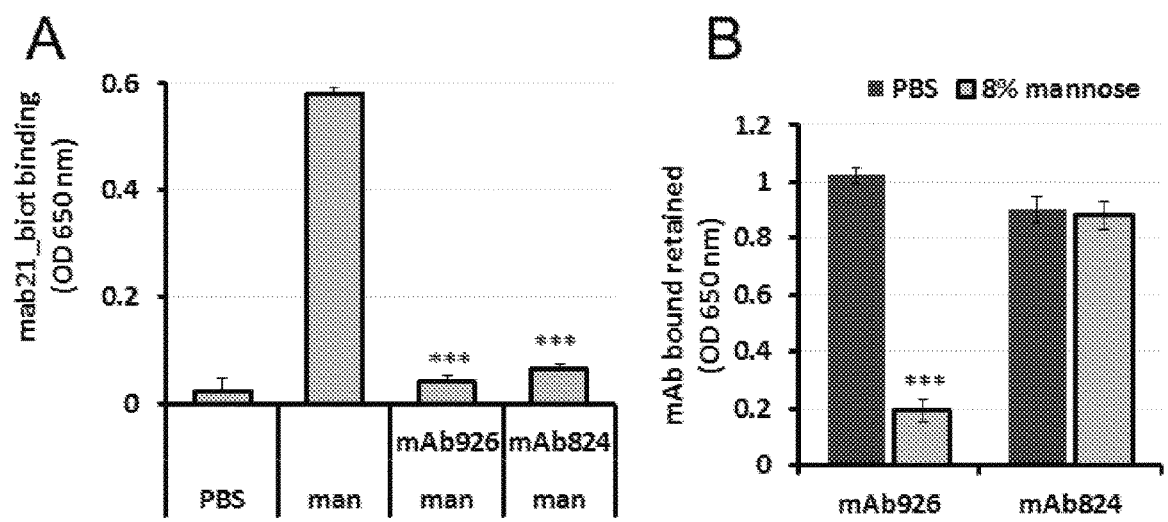
FIG. 6. Comparison of the low affinity conformation-stabilizing mAbs. (A) Binding of the active state-specific mAb21 (biotinylated) in the presence of 0.01% (0.52 mM) mannose to untreated or mAb926- and mAb475-treated fimbrial FimH$^{wt}$. (B) Level of antibodies bound to FimH$^{wt}$ retained after treatment of the antibody-FimH complexes with PBS or 8% (440 mM) mannose for 1 h. Data shown are mean±SEM (n=3 independent experiments). ***, P≤0.0005 (t-test).

Example 6: mAb926 Differs from mAb824 which Allosterically Stabilizes the Low-Affinity State of FimH Considering that mAb926 was found to stabilize the low-affinity conformation of FimH, we determined whether any antibodies from our original panel (Kisiela, et al. 2013) have analogous activity. We found that indeed one of the antibodies, mAb824, can also prevent binding of active state-specific mAb21 to FimH$^{wt}$ in the presence of soluble mannose (FIG. 6A), i.e. mAb824 stabilizes the low-affinity state of the adhesin similar to mAb926. Unlike the latter, however, mAb824 recognized an epitope located away from the mannose-binding pocket (residues G79, S80, Y82, and P91; Table 4) suggesting that the stabilization of the low-affinity conformation of FimH occurs via an allosteric, i.e. away-from-ligand, mechanism. While mannose could not displace mAb824 from FimH$^{wt}$ in SPR experiments (FIG. 18A), SPR studies with mAb824 could not be reliably performed due to difficulties in re-generating the antigen surface upon the mAb824 antibody binding. Thus, the stability of mAb926- and mAb824-FimH$^{wt}$ complexes in the presence of soluble mannose was measured by ELISA. Unlike mAb926, mAb824 is not displaced from FimH$^{wt}$ even at high (8%) concentration of ligand (FIG. 6B). Notably, in the absence of mannose, both antibodies were binding to FimH at the same level upon 4 h-long incubation with PBS (FIG. 18B).

TABLE 4

Mapping of mAb824 epitope using FimH mutant library.

| Mutation | mAb binding relative to wild type* (%) |
|---|---|
| F1L | 99 |
| A2S | 102 |
| P12A | 99 |
| I13S | 98 |
| N46Q | 97 |
| N46A | 103 |
| D47S | 105 |
| Y48A | 104 |
| E50A | 97 |
| I52A | 98 |
| T51A | 98 |
| D54E | 100 |
| L68V | 92 |
| S69C | 65 |
| N70C | 89 |
| N70G | 93 |
| F71A | 105 |
| S72A | 99 |
| T74K | 93 |
| G79R | 4 |
| S80R | 2 |
| S81R | 95 |
| Y82A | 3 |
| P83S | 99 |
| P83R | 98 |
| F84S | 101 |
| P85S | 99 |
| T87A | 107 |
| T90G | 100 |
| T90N | 95 |
| P91A | 98 |
| P91R | 2 |
| R92A | 108 |
| R92D | 99 |
| P104W | 102 |
| I130A | 105 |
| R132D | 96 |
| Q133N | 99 |
| N135I | 109 |
| N136A | 98 |
| Y137A | 97 |
| I138A | 86 |
| S139A | 102 |

*Binding of mAb824 to purified isogenic fimbriae with different mutations in LD of FimH$^{wt}$ was tested as described in Materials and Methods. Predicted mAb824 epitope residues mutation of which reduced the mAb binding >25% (and which also clustered together on FimH crystal structure) are marked in bold type.

These results suggested that while stabilization of the low-affinity conformation of FimH by antibodies could be achieved via an allosteric mechanism, the parasteric mechanism may provide unique properties of interference between the mannose ligand and mAb926 binding, not provided by an allosteric mechanism.

Example 7: mAb926 is superior to the competitive antibody, mAb475, in detaching surface biofilm and protection against urinary tract infection.

Figure 7:
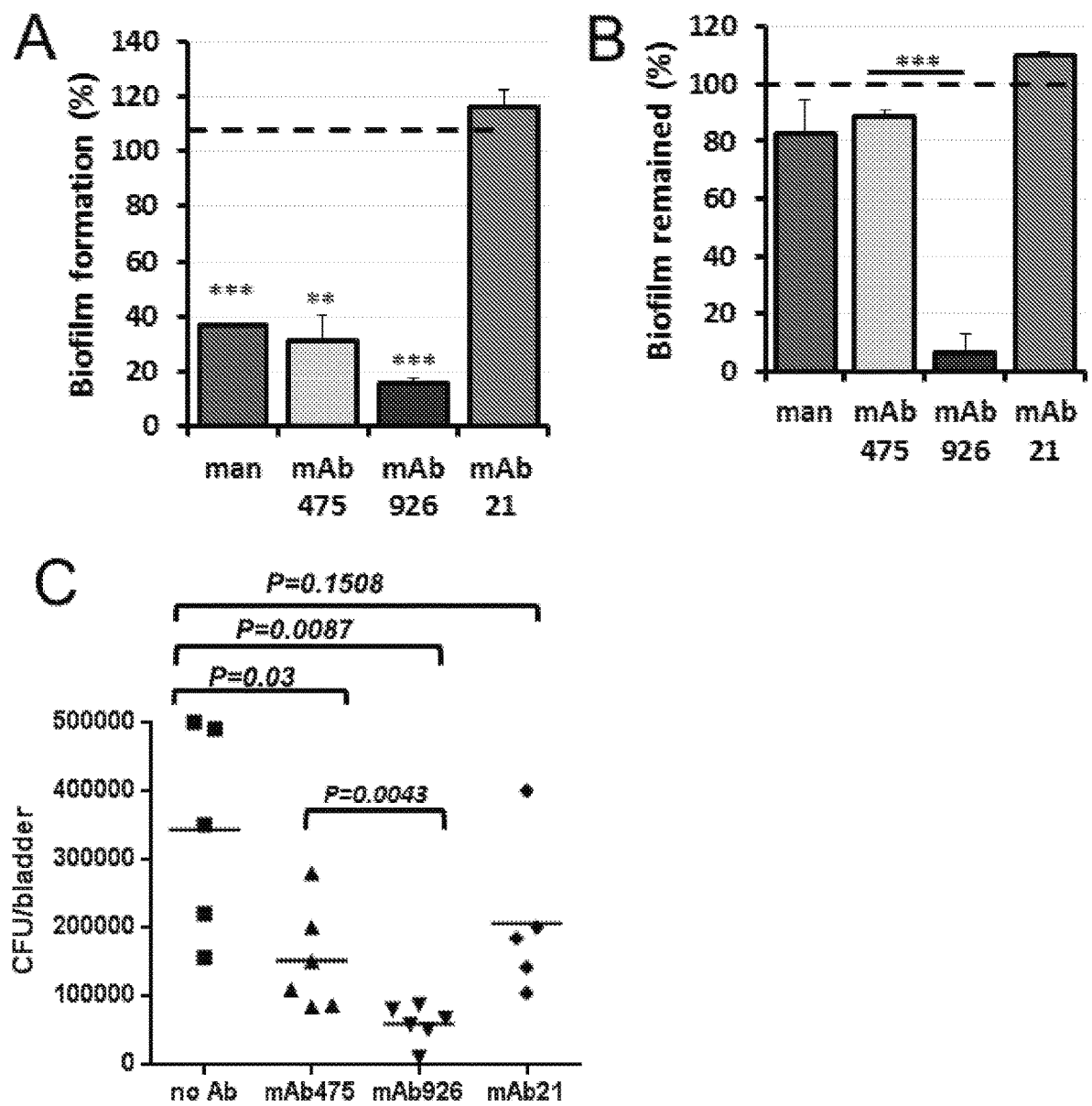
FIG. 7. Effect of mAb926 and mAb475 on biofilm formed by $E.\ coli$ UTI89 on mannan-coated surfaces and bladder infection in mice. (A) Biofilm formation by $E.\ coli$ UTI89 in the presence of 1% mannose or 50 µg/ml monoclonal antibodies. Data (mean±SEM, n=4 independent experiments) are shown relative to the level of biofilm formed in the absence of mannose or antibodies (dashed line). , P≤0.005, *, P≤0.0005 (one sample t-test). (B) Detachment of 16 h-old $E.\ coli$ UTI89 biofilm in the presence of 1% mannose or 50 µg/ml mAbs. Data (mean±SEM, n=3 independent experiments) are shown relative to the level of biofilm detached in the presence of PBS (dashed line). Biofilm was quantified using the crystal violet staining method. ***, P≤0.0005 (t-test). (C) $E.\ coli$ UTI89 recovered from bladders 24 h post transurethral infection of mice. Bacteria, prior to administration into mouse bladders, were pre-incubated with PBS, mAb475, mAb926 or mAb21 for 1 h. Horizontal bars indicate the mean (n=5 or 6 mice per group). P values for indicated datasets were determined using two-tailed Mann-Whitney test.

This Example evaluates the effect of inhibitory antibodies against an *E. coli* biofilm formed on a mannose-coated surface by the model uropathogenic strain UTI89 expressing type 1 fimbriae (Kisiela, et al. 2015). Both mAb475 and mAb926 (as well as soluble mannose), prevented formation of *E coli* biofilm on a mannan-coated surface when they were added to the bacteria prior to growth over the surface (P<0.005), indicating that biofilm formation is dependent on mannose-specific bacterial adhesion (FIG. 7A). However, when we first allowed the surface biofilms to form on a mannan-coated surface overnight and then added the antibodies (or mannose), neither mAb475 nor soluble mannose caused substantial detachment of the surface-attached biofilm (FIG. 7B). In contrast, mAb926 resulted in effective dissolution of the biofilm (93% biofilm reduction vs 12% for mAb475, P<0.0005). In concordance with our previous results from bacterial adhesion assays (Kisiela, et al. 2013), the active state-specific antibody, mAb21, enhanced biofilm formation and decreased dissolution of biofilm formed on a mannan-coated surface (FIGS. 7A and B).

We then compared the antibodies for their ability to block *E. coli* infection in vivo. As shown in FIG. 7C, incubation of *E. coli* UTI89 with mAb926 prior to inoculation of mice via bladder catheter blocked bladder colonization more effectively than mAb475. There was an 83% reduction in bacteria recovered from bladder of mice infected with *E. coli* UTI89 that were pre-treated with mAb926 (FIG. 7C), while inhibition with mAb475 was 52% (P=0.0087). A slight decrease in bacterial load caused by mAb21 did not achieve statistical significance (P=0.1508).

Thus, the non-competitively-inhibiting mAb926 is more effective than is the competitively-inhibiting mAb475 in assays that are most physiologically relevant, such as detachment of biofilms and prevention of bladder infections by uropathogenic *E. coli*.

We have shown that mAb926 has a superior potency to block bacterial adhesion in vitro and decrease bladder colonization in mice when transurethrally administered to the bladder together with bacteria used for the challenge (UPEC strain, UTI89) (FIG. 7C).

We also evaluated protective effects of mAb926 against different UPEC strain, CFT073, upon a passive transfer of the antibody to peritoneal cavity of mice. The intraperitoneal injection was completed 1 day prior and 1 day after challenge with CFT073 *E. coli* (A07 Study for Vaccine candidate, Contract #HHSN2722010000401, Task Order #HHSN27200005, Galveston). In this study, effect of passively transferred mAb926 (raised against FimH $LD^{mut}$) was compared to the action of passively administered mAb21 antibody (raised against FimH $LD^{wt}$), as well as to the effect of active immunizations with the two types of antigen ($LD^{wt}$ and $LD^{mut}$) against which the monoclonal antibodies were raised. Mixtures of antibodies for passive transfer were prepared as 150 µg per mouse doses in 50 µl volumes of sterile HBS. The effect of the antibodies was evaluated in two mice models that included non-diabetic and diabetic C57Bl/6 mice, respectively. Mice injected with incomplete Freund's adjuvant only (IFA) were used as the control (mock) group in each model. Bacterial load in mice urine was analyzed daily over 14-days' time period starting 24 h after bacterial challenge.

As shown in FIGS. 8A and C, passive immunization of non-diabetic mice with mAb926 but not mAb21 resulted in significant decrease of bacterial counts in urine as compared to the mock group starting on day 1 after the challenge: estimated average $\log_{10}$ of bacterial counts in mock mice 2.58±0.3 vs 1.31±0.5 and 2.47±0.5 in mAb926 and mAb21 mice, P=0.009 and P=0.801, respectively. Similar trend continued to be present for up to 10 of 14 days tested after the challenge (FIGS. 8 A and C). On the day 1 and 3 estimated bacterial counts in mAb926-treated mice were also significantly lower as compare to counts from mAb21-treated mice ($\log_{10}$ 1.31±0.5 and 0.99±0.4 vs 2.47±0.5 and 1.89±0.4, P=0.018 and P=0.019, respectively). As observed previously for intraurethral administration of mAbs, the peritoneal injection of mAb21 resulted in somewhat better clearance of bacteria in comparison to mock group, though, the effect of this treatment (similar to active immunization with $LD^{wt}$) did not achieve statistical significance (FIGS. 8A and C). In turn, the effect of passive transfer of mAb926 closely resembled the effect of active immunization with the $LD^{mut}$, against which mAb926 was elicited with both treatments causing significant decrease of bacterial level in urine in comparison to mock group and better clearance of infection (FIGS. 8 A and C). Moreover, the passive transfer of mAb926 also reduced bacterial load in diabetic mice (FIGS. 8 B and C). However, in this model, mice from all treatment groups presented on average much higher bacterial counts in urine than no-diabetic mice and this sustained true over whole time period tested upon challenge (FIGS. 8 B and C). Though, passive immunization of mice with mA926 (or active immunization with $LD^{mut}$) significantly decreased bacterial counts in mice urine in comparison to mock group, there was no significant decrease of bacterial counts for these treatments with time (FIGS. 8 B and C).

Example 8: mAb926 is Active Against Other Enterobacteriaceae that Express Homologues FimH Adhesin

*Klebsiella pneumoniae* is an important opportunistic pathogen frequently causing UTIs, septicemia or respiratory tract infections. Similar to *E. coli*, *Klebsiella pneumoniae* expresses mannose-specific type 1 fimbriae with FimH adhesin being 72-84% homologous to *E. coli* FimH at amino acid sequences level. The sequence alignment revealed that mAb475 and mAb926 epitopes are not targeted by amino acid changes, though presence of amino acid replacement at the position 132 (R to H) in *Klebsiella* binding pocket could indirectly affect the antibodies binding. This especially related to mAb475, which epitope includes neighboring residue from position 133, the residue, important for ligand recognition in *E. coli*. Indeed, fine specificity of the FimH adhesins is somewhat different, as *Klebsiella* FimH in contrast to *E. coli*, shows decreased capability to binds terminally exposed monomannose residues (Stahlhut, et al. 2009).

The analysis of the antibodies binding showed that both anti-*E. coli* FimH antibodies recognized *Klebsiella* FimH (FIG. 9). While mAb926 presented the same level of binding to both FimH adhesins, mAb475 bound to *Klebsiella* FimH variants at lower level than to *E. coli* FimH. Incubation of *Klebsiella* cells with mAb475 and mAb926 significantly reduced bacterial adhesion to plate-coated mannose ligand (RNaseB), with mAb926 substantially outcompeting inhibitory effect of mAb475 (FIG. 10). We next tested whether mAb926 can block formation of biofilm by *Klebsiella* or affect a biofilm that was already formed. As shown in FIG. 11 A, mAb926 effectively inhibited formation of biofilm (76-86% of inhibition, P≤0.0005) by two different *Klebsiella* FimH variants being more potent than soluble mannose that caused 38-67% inhibition. Similar, incubation of 14-h-old biofilm with mAb926 but not mannose or mAb21 caused significant (P=0.0005) destabilization of the biofilm (FIG. 11B).

Thus, the non-competitively-inhibiting mAb926 is effective in blocking adhesion and biofilm formation of *Klebsiella* that expresses homologues FimH adhesin and thus the antibody might be promising anti-infective agent against other Enterobacteriaceae-caused infections.

Example 9: Significance of Antibodies Binding to Just One Loop of the Ligand-Binding Site for Both Inhibition and Reversal of Bacterial Adhesion Via the Novel Parasteric Mechanism Creating antibodies targeting ligand-binding-site epitopes of receptor proteins is a primary goal in the development of protective or therapeutic antibodies. These antibodies are expected to block receptor binding functions by directly competing with the ligand. By definition, for competitive inhibition to occur, the binding pocket cannot be occupied by the ligand at the moment of inhibitor binding (FIG. 12A). Thus, such orthosteric inhibitors cannot reverse ligand binding by triggering detachment of ligand from the pocket, and are ineffective in the presence of high concentrations of endogenous ligand, which limits their utility. The only inhibitors able to detach bound ligand are thought to be those of an allosteric nature that induce a weakly-binding inactive receptor state by signaling a conformational change from the site that is positioned distal to the ligand-binding pocket (FIG. 12B). However, design of allosteric inhibitors is problematic for proteins where conformational regulation is unknown, not existing or complex.

We demonstrated here that the ligand-binding site of a receptor protein provides epitopes for powerful inhibitory antibodies that interfere with ligand binding within the pocket (like orthosteric inhibitors) but in a non-competitive manner (like allosteric inhibitors), via a mechanism that we refer to as parasteric (next-to-ligand) inhibition. Allosteric inhibitors have been described that bind near the pocket (Luo, et al. 2004; Mukund, et al. 2013; Wu, et al. 2007), however, unlike the parasteric inhibitor, they did not bind the ligand-interacting pocket residues themselves. The term 'parasteric inhibition' was suggested previously to highlight at least a theoretical possibility that inhibitor and ligand could bind in close proximity to each other rather than to fully overlapping or distant sites as expected for orthosteric and allosteric inhibitors, respectively (Dissing, et al. 1993). That study was focused on modulation of enzymatic activity of ACP1 by purine modulators, but structural or mechanistic details of the inhibition were not examined. We show here that one of the striking apparent properties of the parasteric antibody is to bind to the binding pocket simultaneously with the ligand and prevent its conversion into the active state (FIG. 12C). In this way, the parasteric concept is also distinct from the concept of inverse agonists, like those shown for the human G-protein coupled receptors, which can stabilize the inactive state of the pocket, but do not bind simultaneously with ligand (Jaakola, et al. 2008; Lebon, et al. 2011).

Parasteric inhibition is potentially applicable to a wide range of receptors. Conformational dynamics of the binding pocket is considered to be an essential property of all ligand-binding proteins (Boehr, et al. 2009; Goh, et al. 2004; Henzler-Wildman and Kern 2007). At least two different conformational states of the binding pocket are proposed to exist for receptor proteins—the active state that binds the ligand strongly and the inactive state that binds the ligand relatively weakly. In many or even the majority of cases, the active state pocket tightens around the ligand relative to the inactive state. For example, the two domains of the maltose binding protein hinge close to increase affinity (Quiocho, et al. 1997; Spurlino, et al. 1991), a 'lid' over the binding site of adenylate kinase closes to prevent substrate exit (Wolf-Watz, et al. 2004), a 'gate' of the plant hormone abscisic acid receptor closes around the hormone ligand (Nilsson, et al. 2008), and the binding pocket of the beta-adrenergic receptor contracts around catecholamines (Lebon, et al. 2011; Warne, et al. 2011). Similarly, the ligand-binding loops of various receptor proteins have been shown to be highly flexible by NMR and FRET analysis (Kim, et al. 2013; Tang, et al. 2007). This suggests that parasteric inhibitors could potentially bind simultaneously with ligand to the more loosely binding open pocket, preventing it from tightening in many different receptor-ligand systems. Notably, many of these receptors undergo only localized conformational dynamics that are not allosteric in nature, so the parasteric mechanism should be applicable to a wider range of receptors than the allosteric mechanism. The wealth of accumulated structural and functional data on different FimH states and the availability of various conformation-specific monoclonal antibodies provided an opportunity to use FimH as a prototype molecule to study dynamics of conformational shifts between active and inactive states and test various types of inhibitors and conformational modulators.

To gain insight into the mAb926 inhibitory mechanism, we turned to the crystal structure of inactive FimH with an open mannose-binding pocket, which was obtained without mannose (Le Trong, et al. 2010). Our previous studies on locking the inactive conformation have suggested that the open pocket of FimH retains some ability to interact with mannose (Le Trong, et al. 2010). Also, studies of others have shown that mutation of one of the mannose-binding residues, Gln133 to Asn, virtually eliminated the binding function of FimH, but mannose still could be co-crystallized with the mutant (Hung, et al. 2002). In the latter structure, mannose retained the same interactions as in the native active pocket with all binding residues except for the N135 and D140 residues that shifted away from the ligand, supporting our conclusion that the latter residues are on a flexible pocket loop. Further support for our model is provided by previous molecular dynamics simulations that predicted that residues F1 and D54 (i.e. those not on the flexible loop) form the strongest interaction with the ligand (Nilsson, et al. 2008). Thus, our model pointing to the dynamic nature of the 133-140 loop is consistent with previous studies.

It remains unclear whether the binding pocket must undergo a shift from the active to the inactive conformation in order for mAb926 (or any parasteric inhibitor in general) to gain access to its epitope when ligand is already bound. In the case of FimH, the 132-140 loop of the pocket that carries mAb926 epitope may transiently shift away from the attached mannose. Indeed, the intrinsic opening rate of maltose-binding protein has been recently shown to determine ligand dissociation (Seo, et al. 2014). Another possible scenario for mAb926 action could involve its intermediate binding to the active conformation of the mannose-occupied pocket of FimH via a portion of the epitope that does not involve the mannose-binding residues N135 and D140. In turn, the possible intermediate step of binding could facilitate the full opening of the flexible loop, thus de-activating the active state. Indeed, mutation of mAb926 epitope residues that are not involved in hydrogen bonding with ligand and facing outside the pocket cleft (152, N136 and Y137) did not decrease or had only minimal effect on mannose ligand binding (Kisiela, et al. 2013) suggesting that they could be accessible for interactions with the antibody even if the pocket is occupied by the ligand. Further studies are needed to elucidate the structural details of the inhibitory action of mAb926 and that of other potential parasteric inhibitors.

Although interaction of the lectin domain with the pilin domain in FimH allosterically facilitates the inactive conformation of the binding pocket, soluble pilin domain failed to stabilize the low affinity state of the adhesin (Aprikian, et al. 2007). In this study, however, we found an antibody, mAb824 that appears to prevent shifting of FimH$^{wt}$ from the low- to high-affinity state in an apparently allosteric manner by binding an epitope located away from the binding pocket. This epitope is positioned on a side of the split sheet of the lectin domain of FimH that may be a critical region in the conformational pathway of the switch, but details of mAb824 action require further investigation. Importantly, we observed that, unlike mAb926, mAb824 is not displaced from FimH by soluble mannose suggesting that the ligand-induced conformational shift in FimH cannot overcome the conformation-stabilizing effect of mAb824. It is plausible to expect that at least in some receptor proteins, allosteric antibodies that are bound to the inactive conformation might be displaced by the ligand-induced activation of the protein and conversely that ligand bound to the active conformation might be displaced by allosteric inhibitory antibodies. However, allosteric antibodies are fundamentally different from parasteric antibodies in a way that is likely to affect the issue of induced dissociation. Allosteric antibodies bind to sites that are distinct from, and relatively weakly coupled to, the binding site (Christopoulos 2002). This means that the antibody epitope can be in the inactive conformation while the binding site is in the active conformation. In contrast, a parasteric antibody by our definition has an epitope that to some extent overlaps with the binding site, so that binding kinetics must be changed if the antibody binds, and vice versa. We hypostatize that this difference explains the lack of mAb824 displacement by mannose from FimH but more extensive studies of mAb824 are needed to address this question. Thus, although mAb926 binding to FimH has an allosteric effect on the lectin domain, its inhibition of mannose-binding is not via the allosteric mechanism per se and is fundamentally distinct from the action exerted by mAb824 or other classic allosteric inhibitors described for other receptor-ligand interaction systems (Doern, et al. 2009; Hino, et al. 2012; Luo, et al. 2004).

The model of non-competitive inhibition by mAb926 implies that the antibody and the ligand can bind simultaneously to FimH, i.e. form at least a transient FimH-mannose-mAb926 complex. This is experimentally supported by the observation that mannose accesses the FimH pocket occupied by mA926 but not by mAb475, resulting in unbinding of the former. The exact mechanism of how the three-way complex forms and why it is unstable is unclear, but is likely that antibody is eluted from FimH due to a structural distortion or steric hindrance caused by ligand binding. Reciprocally then, the co-binding property of mAb926 would lead to ligand unbinding when the receptor is already occupied by the ligand. Indeed, we observed that bacterial biofilm formed on a mannose-coated surface can be effectively detached only by mAb926 compared with the relatively minor effect of mAb475 antibody or even high concentrations of soluble mannose. To our knowledge, mAb926 is the only antibody shown to dissolve a bacterial biofilm.

The phenomenon of apparent simultaneous binding of the inhibitory mAb926 and the mannose ligand in spite of overlapping binding sites, makes it distinct from both the orthosteric and allosteric inhibitors, providing the rationale for defining a novel, parasteric mechanism of ligand binding inhibition. The advantage of parasteric inhibitors vs orthosteric inhibitors is that the former would be more potent in unbinding the ligand from the binding pocket and more effective in the presence of high concentrations of endogenous ligands. Either effect can explain the significantly stronger inhibition by mAb926 relative to the competitive inhibitor mAb475, and the superior ability of mAb926 to block FimH-mediated mouse bladder colonization. Although we demonstrated that the ligand can enter the binding pocket with bound mAb926 and in fact displace the antibody, this only occurred at very high, non-physiologic concentrations, and would not compromise the effectiveness of the antibody as a ligand-binding inhibitor. Many bacterial adhesins mediate shear-enhanced adhesion similar to FimH (Ding, et al. 2010; George, et al. 2006; Nilsson, et al. 2006a; Tchesnokova, et al. 2010), suggesting that they may also undergo conformational changes and be candidates for parasteric inhibition. The advantage of parasteric inhibitors vs allosteric inhibitors is that the effectiveness of the parasteric inhibition is not limited by weak coupling of the allosteric site to the ligand binding site, and that parasteric inhibition does not require the receptor to be allosteric. In comparison to allosteric inhibitors which present difficulties for rational design due to lack of knowledge of the location of allosteric sites, development of parasteric inhibitors may be more universally applicable to any protein with defined ligand binding sites, whether or not the protein is allosteric.

The epitope of mAb926 appears to be highly conserved. The sequence analysis of the epitope region in 488 different fimH alleles from 4271 strains of E. coli of various origin (intestinal, extraintestinal and environmental) showed that out of 488 alleles, only 1 allele (5 strains) had variability in one of the epitope position: D140. However, this allele was extremely rare (present in 5 strains out of >4,000 isolates) indicating that mAb296 can be universally potent against great variety of E. coli isolates. Moreover, this antibody effectively blocked adhesion and biofilm formation of Klebsiella pneumoniae. Klebsiella pneumoniae, an important opportunistic pathogen frequently causing UTIs, septicemia or respiratory tract infections expresses mannose-specific type 1 fimbriae with FimH adhesin being 72-84% homologous to E. coli FimH (at amino acid sequences level). Though the binding pocket of Klebsiella FimH is somewhat different from E. coli (Stahlhut, et al. 2009), still epitope of mAb926 sustained unchanged in comparison to E. coli, being identical in more than 100 different fimH alleles from >540 Klebsiella strains analyzed. This suggested that mAb926 might be potent inhibitor also against other Enterobacteriaceae that express homologues FimH adhesin.

Taken together, our findings suggest that antibodies binding to just one loop of the ligand-binding site have the potential to be very effective for both inhibition and reversal of bacterial adhesion via the novel parasteric mechanism. The binding pocket side loops of bacterial adhesins appear to be good targets for generation of antibodies with such potential. The observation that the mAb926 epitope is largely formed by a single loop makes this loop a good candidate immunogen for induction of parasteric antibodies using synthetic cyclic peptides. Loop-shaped epitopes have been shown to be extremely potent as synthetic peptide-based vaccines due to their structural properties when synthesized in circular form that not only well mimic the native epitopes but also exhibit extremely high stability as immunogenic agents (Hoogerhout, et al. 1995; Misumi, et al. 2003).

Example 10: Monoclonal Antibody Production and Purification

Hybridoma cells producing mice antibodies, mAb475, mAb824, mAb926 and mAb21, were grown in IMDM media (Lonza) complemented with 10% FBS (Gibco, #10082147), Pen/Strep (Gibco, 315140-122) and Sodium Pyruvate (Gibco, #11360). The antibodies were purified from hybridoma cell culture supernatants using protein G-agarose (Millipore) according to manufacture recommendations followed by FPLC purification using 16/60 Superdex 75 column (GE Healthcare). All FPLC purification steps were performed in HBS and the antibodies at the final concentration 5-10 mg/ml were stored at 4° C.

Example 11: Sequencing of V-Region of mAb Light and Heavy Chains

Total mRNA was isolated from hybridoma cells using RNase Mini kit (Qiagen, #74104), followed by cDNA synthesis with the Omniscript RT kit (Qiagen) and oligo dT primer (Qiagen). The V-regions were PCR amplified using 2 µL from the 20-µL RT reaction volume with the following primers: forward:
VL4 (mAb475): CCAGTTCCGAGCTCCAGATGAC-CCAGTCTCCA (SEQ ID NO: 9);
VL5 (mAb926): CCAGATGTGAGCTCGTGATGAC-CCAGACTCCA (SEQ ID NO: 10);
VH1 (mAb475 and mAb926): AGGTCCAGCTGCTC-GAGTCTGG (SEQ ID NO: 11); and
reverse: VLr (mAb475 and mAb926): GCGCCGTCTA-GAATTAACACTCATTCCTGTTGAA (SEQ ID NO: 12); and
VH3r(IgG1-specific):
AGGCTTACTAGTACAATCCCTGGGCACAAT (SEQ ID NO: 13).
Purified PCR products were subjected to sequencing by Genewiz Inc. (Seattle). Germline origin of anti-FimH antibodies was determined based on the V-region sequence of their light and heavy chains using IMGT/V-Quest software (available online) (Brochet, et al. 2008; Giudicelli, et al. 2011).

Example 12: Antibody Epitope Mapping

Mapping of mAb926 and mAb824 epitopes was performed as described previously (Kisiela, et al. 2013). Briefly, the antibodies were tested for the ability to recognize purified isogenic fimbriae carrying different mutations in LD of FimH. Parental (not mutated) fimbriae were used as a reference against which binding of the antibodies to all other mutant fimbriae was normalized. Epitopes of mAb926 and mAb824 were mapped using the high affinity FimH variant ($FimH^{wt:(188-201)FocH}$, (Aprikian, et al. 2007) and the low affinity FimH variant (FimH$^{wt}$), respectively.

Example 13: Bacterial Strains

The *Escherichia coli* clinical isolate UTI89 and recombinant strains of *E. coli* K12 expressing type 1 fimbriae with different structural FimH variants were previously described (Aprikian, et al. 2007; Liu, et al. 2012; Tchesnokova, et al. 2008). Briefly, the recombinant strain of *E. coli* K12 (AAEC191A) carries pPKL114 plasmid containing the entire fim gene cluster from the *E. coli* strain K12, but with the inactivated fimH gene. For type 1 fimbriae expression, pPKL114 plasmid harboring bacteria were transformed with isogenic pGB2-24-based plasmids carrying different alleles of the fimH gene. The AAEC191A recombinant strain was also used to produce type 1 fimbriae carrying *Klebsiella pneumoniae* FimH (Stahlhut et al., 2009) including FimH wild type (FimH$^{wt}$) and S62A mutant (FimH$^{S62A}$). The *Klebsiella pneumonie* fimH mutant complemented with different fimH variants was described previously (Struve, et al. 2008).

Example 14: ELISA Assays

Microtiter plate wells were coated with purified fimbriae (Kisiela, et al. 2013) at concentration 0.1 mg/ml (unless stated otherwise) in 0.02 M NaHCO$_3$ buffer for 1 h at 37° C. The wells were washed with PBS and quenched for 20 min with 0.2% BSA in PBS. To test the effect of mannose on monoclonal antibody binding, immobilized fimbriae were incubated with serial dilutions of pure mAbs in the absence or presence of 52 mM α-methyl-D-mannopyranoside (amm, hereinafter also termed 'mannose'). Bound antibodies were detected with a 1:5,000 diluted HRP-conjugated goat anti-mouse antibody (Bio-Rad). The reaction was developed using 3,3',5,5'-tetramethylbenzidine (TMB, KPL), and absorbance was read at 650 nm. EC$_{50}$ values were determined by non-linear regression curve fitting using Prism 6.0 software (GraphPad, La Jolla, Calif.) for each antibody independently.

To test the effect of antibodies on the adhesin conformation, immobilized fimbriae were incubated with 50 µg/ml pure antibodies, or 52 mM mannose for 1 h and then 0.5 µg/ml biotinylated mAb21 was added to wells. After washing, binding of biotinylated mAbs was detected using a 1:5,000 diluted HRP-conjugated streptavidin (Sigma-Aldrich). In some experiments, surface-immobilized fimbriae were first incubated with 0.5 µg/ml biotinylated mAbs (in the absence or presence of 52 mM mannose) followed by incubation with purified mAbs 50 µg/ml for 1 h.

To test the effect of ligand on the stability of FimH-antibody complexes, antibodies at concentration 0.4 µg/ml were first bound to surface-immobilized fimbriae, followed by incubation with 8% mannose, or PBS for 1-4 h time.

Example 15: Surface Plasmon Resonance (SPR) Analyses

SPR analyses of mAb926, mAb475 and mAb824 binding to FimH$^{wt}$ followed by the absence or presence of 1% (w/v) mannose were conducted at 25° C. in a running buffer (RB) of HBS-EP+ (0.01 M Hepes pH 7.4, 0.15 M NaCl, 3 mM EDTA, 0.05% (v/v) Surfactant P20) with 0.1 mg/mL BSA on a Biacore T100 system (GE Healthcare). Using standard amine coupling chemistry, ~2000 RUs of FimH$^{wt}$ fimbriae were amine-coupled at 20 µg/mL in 10 mM glycine, pH 2.5 to 2 flow cells of a Series S CM5 chip (GE Healthcare). Two reference surfaces were prepared by activating and deactivating flow cells without the addition of protein. Duplicate (single for mAb824) samples at a single concentration were injected at a flow rate of 10 UL/min using a "dual" injection command in the T100 control software (v2.0.4) with injection 1 at 5 mins, injection 2 at 10 mins and a final dissociation time of 1 min. MAb alone curves were generated by injecting mAb followed by an injection of RB and double referenced (Myszka 1999) by subtracting a dual injection of RB followed by RB. mAb+mannose curves were generated by injecting mAb (in RB without mannose) followed by an injection of RB with 1% mannose and double referenced by subtracting a dual injection of RB followed by RB with 1% mannose. Optimal regeneration was achieved by injection of either one (for mAb926) or 2 (for mAb475) 30 second pulses of 10 mM glycine, pH 1.5 at a flow rate of 50 L/min followed by a 2 min buffer stabilization phase. Optimal regeneration conditions for mAb824 sample binding were not found, and so required the generation of two FimH$^{wt}$ fimbriae surfaces with only a single mAb824 injection on each. MAb926 and mAb475 injections with and without mannose were run on each FimH$^{wt}$ fimbriae surface prior to the mAb824 injection in order to match mAb824 binding surfaces as closely as possible, as well as to provide a control for comparison. Sensorgrams were double-referenced in Scrubber 2.0b software (BioLogic Software), saved as text files, and re-plotted in Prism GraphPad 6 software.

To determine apparent kinetic rate and equilibrium binding constants, FimH$^{wt}$ fimbriae were amine-coupled as noted above to a density of 1300 RUs, with an activated/deactivated surface used as reference. Serial 2-fold dilutions of analyte starting at 12.5 nM (mAb926) or 200 nM (mAb475), and buffer blanks were injected in random order and run in duplicate in HBS-EP+ with 0.1 mg/mL BSA at a flow rate of 30 μL/minute with 700 s of association and 1200 s of dissociation. Surfaces were regenerated with either one 30 s injection (mAb926) or two 30 s injections (mAb475) of 10 mM glycine, pH 1.5 at 50 μL/minute followed by 2 mins of buffer stabilization. Double-referenced data were fit with a 1:1 binding model with BIAevaluation 2.0.4 software (GE Healthcare).

Example 16: Bacterial Adhesion

Microtiter 96-well plates were coated with 20 μg/ml of yeast mannan or RNaseB (Sigma-Aldrich) in 0.02 M NaHCO$_3$ buffer at pH 9.6. The wells were quenched with 0.2% bovine serum albumin (BSA, Sigma-Aldrich) in PBS for 20 min. Bacteria expressing FimH adhesin (OD=1 or OD=2) were first preincubated with different concentrations of mAbs for 1 h at 37° C. and then allowed to adhere to ligand-coated surface for another 1 h. After an extensive washing with PBS, plates were dried and bound bacteria were stained with 0.1% crystal violet (Becton Dickinson) for 20 min at room temperature (RT). The wells were washed with water and 50% ethanol was added to the wells. The absorbance was measured at 600 nm.

Example 17: Biofilm Formation Assay

Microtiter 96-well plates were coated with 20 μg/mL of yeast mannan or RNaseB (Sigma-Aldrich) in 0.02 M NaHCO$_3$ buffer at pH 9.6. Bacterial strains grown overnight in 3 ml LB media were spun and washed 1× with minimal essential media (MEM, Difco). Bacterial suspensions in MEM, at final concentration OD=0.2, were added to mannan-coated wells in the absence and presence of 52 mM mannose or 50 μg/ml mAbs and incubated 16 h at RT without shaking. After washing with PBS, formed biofilms were stained with 0.1% (v/v) crystal violet (Becton Dickinson) as described above for bacterial adhesion assay. For biofilm detachment, 16 h-old biofilm produced by *E. coli* UTI89 on mannan-coated microtiter plates was washed 3 times with PBS and incubated in the absence or presence of 1% mannose or 50 μg/ml mAbs at RT with mild shaking. The wells were washed 3 times with PBS and stain for biofilm detection as described above.

Example 18: Mouse Experiments with Transurethral Injection of the Antibodies

Infection of 10- to 11-week-old C57BL/6 female mice was performed as described elsewhere (Kisiela, et al. 2013). Briefly, bacteria were grown in LB medium without shaking for 48 h, harvested, washed twice in PBS and resuspended in PBS at a final concentration of $10^8$ CFU per ml. Bacteria were pretreated with 500 μg/ml mAbs for 1 h at 37° C. prior to inoculation. Mice were anesthetized with ketamine/xylazine and twenty-five microliters of mAb-pretreated bacteria in PBS were inoculated transurethrally into mouse bladders via catheter. After 24 h, mice were sacrificed and bladders were aseptically removed and homogenized in 1 mL PBS. Serial dilutions were plated and total bacterial load per bladder was calculated. Statistical significance was determined using two-tailed Mann-Whitney test (GraphPad Prism 6.0 software, La Jolla, Ca).

Example 19: Non-Diabetic and Diabetic Mice Model for Passive Immunization

Diabetic state in C57Bl/6 mice was induced by the 4 days-treatment with streptozotocin (STZ) by intraperitoneal injection. Groups of 100 C57Bl/6 mice were randomly divided into 5 groups of ten for diabetic and for non-diabetic states respectively. One group of each condition was subcutaneously injected with the adjuvant alone (mock), 15 μg of LD$^{mut}$ or 15 μg of LD$^{wt}$ (4 and 1 week before a challenge), with two other groups receiving 150 μg of mAb926 or mAb21 by intraperitoneal injection (1 day prior and 1 day after the challenge). Mice were challenged with CFT073 UPEC strain ($1 \times 10^6$ cfu/50 μl per mouse) via intraurethral catheterization under isoflurane anesthesia. Bacterial load in mice urine was analyzed daily over 14-days' time starting 24 h after bacterial challenge. Genomic bacterial load was quantified in each urine sample (10 μl) by qPCR. Statistical analysis of the data was performed using the Generalized Estimating Equation model (GEE) (xtgee command in STATA software, StataCorp. 2015. *Stata Statistical Software: Release* 14. College Station, Tex.: StataCorp LP). Overall, 1400 observations were made for 100 mice over 14 days. Out of 1,400 total 237 observations were missing (no urine provided) and were excluded from subsequent analysis. The mice ID were set as a panel variable, treatment type and days as predictor variables with interaction allowed between them; and *E. coli* counts as an outcome variable. To account for the heteroscedasticity and non-linearity we performed analysis of log-transformed *E. coli* counts. For $\log_{10}$ transformation, zero counts (*E. coli* not detected) were replaced with value 1. The data for diabetic and non-diabetic mice were fitted separately. The Wald's test was used to calculate inference of the regression parameters using naive standard errors. For bacterial counts from diabetic mice, the residuals analysis showed the presence of non-influential outliers (that represented occasional lack of *E. coli* DNA in urine) that were excluded from the study to satisfy the request for normality of distribution of the dependent variable from independent. After exclusion of outliers, 617 (out of initial 673, 91.6%) observations were analyzed using same model.

Example 20: Modeling and Visualization of Protein Structure

To dock α-D-mannose to the binding site of the inactive conformation of FimH, the crystal structure of the lectin domain (residues 1-158, with PDB code 3JWN) was aligned onto the high affinity structure of FimH lectin domain (PDB code 1UWF) followed by minimization of the RMSD of residues 1 to 6 and 44 to 48. The coordinates of mannose which are present in 1UWF structure were then used to create a complex between LD in low affinity conformation and the ligand. The entire system was then subjected to 100 steps of steepest descent minimization in vacuo and 500 steps of conjugate gradient minimization in a dielectric continuum using the program CHARMM.13 (Brooks, et al. 2009) and PARAM22 force field (MacKerell, et al. 1998). Based on published structural data, (Bouckaert, et al. 2005; Hung, et al. 2002; Wellens, et al. 2008), the mannose-ring retains the same position and makes the same network of hydrogen bonds in the pocket, regardless the nature of mannosylated ligand (i.e α-D mannose, alkyl-derivatives of the mannose or oligomannose substrate). Thus, for simplicity, only the mannose-ring of α-D mannose was modeled and is presented in FimH structures.

In the 1UWF structure, α-D mannose was modeled in by alignment with the sugar ring of the mannose residue of the original crystal structure. The spatial distribution of amino acid residues involved in mAb epitopes and distances between atoms forming hydrogen bonds and mannose ligand in 3JWN and 1UWF structures were measured using the molecular visualization software program PyMOL (DeLano Scientific LLC).

Example 21: Statistics and Data Analysis

All values, unless otherwise indicated, are expressed as mean and SEM. Statistical significance was determined by two-tailed student test using Prism 6.0 software (GraphPad, La Jolla, Ca).

The receptor occupancy by antibody in the presence of mannose was calculated from the equation:

$$EC_{50}^{ratio} = \frac{1 + \frac{[M]}{K_D}}{1 + \alpha \frac{[M]}{K_D}} \quad \text{(Kenakin 2004)}$$

where, α is a cooperativity factor for mannose and antibody, [M] is mannose concentration and $K_D$ is its equilibrium constant. For the strongest possible negative cooperativity (if mannose and antibody are direct competitors) α=0 and $$EC_{50}^{ratio} = 1 + \frac{[M]}{K_D}.$$

As the dissociation constant for mannose and fimbrial FimH$^{wt}$ is 298±50 μM (Tchesnokova, et al. 2008), and antibody binding was tested at a 52 mM concentration of mannose, the expected $EC_{50}$ ratio for competitive binding is 175±30.

REFERENCES

Aprikian, P., et al., 2007, J Biol Chem 282(32):23437-46.
Avlani, V. A., et al., 2007, J Biol Chem 282(35):25677-86.
Boehr, D. D., R. Nussinov, and P. E. Wright, 2009, Nat Chem Biol 5(11):789-96.
Bouckaert, J., et al., 2005, Mol Microbiol 55(2):441-55.
Brochet, X., M. P. Lefranc, and V. Giudicelli, 2008, Nucleic Acids Res 36(Web Server issue):W503-8.
Brooks, B. R., et al., 2009. J Comput Chem 30(10):1545-614.
Carlson, K. E., et al., 1997, Biochemistry 36(48):14897-905.
Chen, S. L., et al., 2009, Proc Natl Acad Sci USA 106(52): 22439-44.
Chen, W., et al., 2012, J Cell Biol 199(3):497-512.
Choudhury, D., et al., 1999, Science 285(5430):1061-6.
Christopoulos. A., 2002, Nat Rev Drug Discov 1(3):198-210.
Connell, I., et al., 1996, Proc Natl Acad Sci USA 93(18): 9827-32.
Csermely, P., R. Palotai, and R. Nussinov, 2010, Trends Biochem Sci 35(10):539-46.
Ding, A. M., et al., 2010, Appl Environ Microbiol 76(4): 1294-7.
Dissing, J., B. Rangaard, and U. Christensen, 1993, Biochim Biophys Acta 1162(3):275-82.
Doem, A., et al., 2009, J Biol Chem 284(15):10254-67.
Duan, X., et al., 2001, J Mol Biol 306(5):1115-26.
Ehlert, F. J., 1988, Mol Pharmacol 33(2):187-94.
George, N. P., et al., 2006, Arterioscler Thromb Vasc Biol 26(10):2394-400.
Gianni, S., J. Dogan, and P. Jemth, 2014, Biophys Chem 189:33-9.
Giudicelli, V., X. Brochet, and M. P. Lefranc, 2011, ICold Spring Harb Protoc 2011(6):695-715.
Goh, C. S., D. Milburn, and M. Gerstein, 2004, Curr Opin Struct Biol 14(1):104-9.
Hatzakis, N. S., 2014, Single molecule insights on conformational selection and induced fit mechanism. Biophys Chem 186C:46-54.
Henzler-Wildman, K., and D. Kern, 2007, Nature 450 (7172):964-72.
Hino, T., et al., 2012, Nature 482(7384):237-40.
Hoogerhout, P., et al., 1995, Infect Immun 63(9):3473-8.
Hung, C. S., et al., 2002, infection. Mol Microbiol 44(4): 903-15.
Jaakola. V. P., et al., 2008, Science 322(5905):1211-7.
Jones, C. H., et al., 1995, Proc Natl Acad Sci USA 92(6): 2081-5.
Kenakin, T., 2004, Mol Interv 4(4):222-9.
Kim, E., et al., 2013, Nat Chem Biol 9(5):313-8.
Kisiela, D. I., et al., 2015, PLoS Pathog 11(5):e1004857.
Kisiela. D. I., et al., 2013. Proc Natl Acad Sci USA 110 (47):19089-94.
Kisielius, P. V., et al., 1989, Infect Immun 57(6):1656-62.
Krogfelt, K. A., H. Bergmans, and P. Klemm, 1990, Infect Immun 58(6):1995-8.
Le Trong, I., et al., 2010, Cell 141(4):645-55.
Lebon, G., et al., 2011, Nature 474(7352):521-5.
Liu. Y., T. M. EI-Achkar, and X. R. WVu, 2012. Biol Chem 287(20):16365-78.
Luo, B. H., et al., 2004, J Biol Chem 279(26):27466-71.
Ma, Q., et al., 2014, Protein Sci 23(7):932-9.
MacKerell, A. D., et al., 1998, J Phys Chem B 102(18): 3586-616.
Martinez, J. J., et al., 2000, EMBO J 19(12):2803-12.
Melcher, K., et al., 2009, Nature 462(7273):602-8.
Misumi, S., et al., 2003, J Biol Chem 278(34):32335-43.
Mukund, S., et al., 2013, J Biol Chem 288(50):36168-78.
Myszka, D. G., 1999, J Mol Recognit 12(5):279-84.

Nilsson, L. M., et al., 2006a, Appl Environ Microbiol 72(4):3005-10.
Nilsson, L. M., et al., 2008, Structure 16(7):1047-58.
Nilsson, L. M., et al., 2006b, J Biol Chem 281(24):16656-63.
Phan, U. T., T. T. Waldron, and T. A. Springer, 2006, Nat Immunol 7(8):883-9.
Quiocho, F. A., J. C. Spurlino, and L. E. Rodseth, 1997, Structure 5(8):997-1015.
Rasmussen, S. G., et al., 2011, Nature 469(7329):175-80.
Remington, Joseph P, and Alfonso R Gennaro, 1990, Remington's pharmaceutical sciences. Volume 18th ed: Mack Publishing Co..
Seo, M. H., et al., 2014, Nat Commun 5:3724.
Silva, D. A., et al., 2011, PLoS Comput Biol 7(5):e1002054.
Sooriyaarachchi, S., et al., 2010, J Mol Biol 402(4):657-68.
Spurlino, J. C., G. Y. Lu, and F. A. Quiocho, 1991, J Biol Chem 266(8):5202-19.
Stahlhut, S. G., et al., 2009, J Bacteriol 191(21):6592-601.
Struve, C., M. Bojer, and K. A. Krogfelt, 2008, Infect Immun 76(9):4055-65.
Swinney, D. C., 2004, Nat Rev Drug Discov 3(9):801-8.
Swinney, D. C., 2006, Curr Top Med Chem 6(5):461-78.
Tang, C., C. D. Schwieters, and G. M. Clore, 2007, Nature 449(7165):1078-82.
Tchesnokova, V., et al., 2008, J Biol Chem 283(12):7823-33.
Tchesnokova, V., et al., 2010. Mol Microbiol 76(2):489-502.
Wagner, D. A., and C. Czajkowski, 2001, J Neurosci 21(1):67-74.
Warne, T., et al., 2011, Nature 469(7329):241-4.
Wellens, A., et al., 2008, PLoS One 3(4):e2040.
Wolf-Watz, M., et al., 2004, Nat Struct Mol Biol 11(10):945-9.
Wu, Y., et al. , 2007, Proc Natl Acad Sci USA 104(50):19784-9.

Throughout this application various publications are referenced. The disclosures of these publications in their entireties are hereby incorporated by reference into this application in order to describe more fully the state of the art to which this invention pertains.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A composition comprising an antibody that specifically recognizes and binds uropathogenic *Escherichia coli* (*E. coli*) fimbrial adhesin FimH and is capable of preventing colonization of a surface by uropathogenic *E. coli*, wherein the antibody comprises:
   (a) a light chain variable region comprising an amino acid sequence selected from the group consisting of SEQ ID NO: 1, SEQ ID NO: 3, and sequences at least 90% identical thereto, wherein the light chain variable region comprises a CDR1 sequence comprising QNVSN (residues 27-31 of SEQ ID NO: 1) or QNIVHNNGNTY (residues 27-37 of SEQ ID NO: 3), a CDR2 sequence comprising SAS (residues 49-51 of SEQ ID NO: 1) or KVS (residues 55-57 of SEQ ID NO: 3), and a CDR3 sequence comprising QQNSSFPFT (residues 88-96 of SEQ ID NO: 1) or FQGSHVPFT (residues 94-102 of SEQ ID NO: 3); and
   (b) a heavy chain variable region comprising an amino acid sequence selected from the group consisting of SEQ ID NO: 2, SEQ ID NO: 4, and sequences at least 90% identical thereto, wherein the heavy chain variable region comprises a CDR1 sequence comprising GYAFSSYW (residues 26-33 of SEQ ID NO: 2) or GYTSTNYW (residues 26-33 of SEQ ID NO: 4), a CDR2 sequence comprising IYPRDGDT (residues 51-58 of SEQ ID NO: 2) or INPTSGYT (residues 51-58 of SEQ ID NO: 4), and a CDR3 sequence comprising EVGRGFYGMDY (residues 97-107 of SEQ ID NO: 2) or ARGVIRDF (residues 97-104 of SEQ ID NO: 4).

2. The composition of claim 1, wherein the antibody inhibits bacterial adhesion to a mannose-coated surface with an IC50 less than one.

3. The composition of claim 1, wherein the amino acid sequence of the light chain variable region has at least 95% identity with SEQ ID NO: 1 or 3.

4. The composition of claim 1, wherein the amino acid sequence of the heavy chain variable region sequence has at least 95% identity with SEQ ID NO: 2 or 4.

5. The composition of claim 1, wherein the amino acid sequence of the light chain variable region is selected from the group consisting of: SEQ ID NO: 1, 3, 5, and 7.

6. The composition of claim 1, wherein the amino acid sequence of the heavy chain variable region is selected from the group consisting of: SEQ ID NO: 2, 4, 6, and 8.

7. The composition of claim 1, wherein the amino acid sequence of the light chain variable region is SEQ ID NO: 3.

8. The composition of claim 1, wherein the amino acid sequence of the heavy chain variable region is SEQ ID NO: 4.

9. The composition of claim 1, wherein the antibody further comprises a heterologous sequence.

10. The composition of claim 1, wherein the antibody is one or more of a polyclonal antibody, a monoclonal antibody, a humanized antibody, a human antibody, an antibody derivative, a veneered antibody, a diabody, an antibody derivative, a recombinant human antibody, a chimeric antibody, or an antibody fragment.

11. The composition of claim 1, wherein the antibody is a monoclonal antibody.

12. The composition of claim 1, further comprising a carrier.

13. A method to inhibit infection of a cell by uropathogenic *E. coli*, comprising administering to a tissue infected with the uropathogenic *E. coli* comprising contacting the cell with an effective amount of a composition of claim 1, thereby inhibiting infection of the cell.

14. A method to treat a bacterial infection in subject in need thereof, wherein the subject is infected with uropathogenic *E. coli, Klebsiella oxytoca,* or *Klebsiella pneumoniae*, the method comprising administering to the subject an effective amount of a composition of claim 1, thereby treating a bacterial infection in the subject.

15. The method of claim 14, wherein the bacterial infection is colitis or sepsis.

16. A method of treating, delaying the onset of, or reducing the severity of inflammatory bowel disease (IBD) in a subject, the method comprising administering to the subject an effective amount of a composition claim 1, thereby treating, delaying the onset of, or reducing the severity of IBD in the subject.

17. The method of claim 13, wherein the administering is by subcutaneous, topical, transdermal, intravenous, oral, or intracolonic administration.

18. A method of displacing mannose from the binding pocket of uropathogenic *E. coli, Klebsiella oxytoca*, or *Klebsiella pneumoniae* fimbrial adhesin FimH, the method comprising contacting the binding pocket with a composition of claim 1.

19. The method of 14, wherein the administering is by subcutaneous, topical, transdermal, intravenous, oral, or intracolonic administration.

20. The method of 16, wherein the administering is by subcutaneous, topical, transdermal, intravenous, oral, or intracolonic administration.

* * * * *